(12) United States Patent
Lang et al.

(10) Patent No.: US 6,811,310 B2
(45) Date of Patent: Nov. 2, 2004

(54) METHODS AND DEVICES FOR ANALYSIS OF X-RAY IMAGES

(75) Inventors: Philipp Lang, Lexington, MA (US); Daniel Steines, Palo Alto, CA (US)

(73) Assignee: Imaging Therapeutics, Inc., San Mateo, CA (US)

( * ) Notice: Subject to any disclaimer, the term of this patent is extended or adjusted under 35 U.S.C. 154(b) by 0 days.

(21) Appl. No.: 10/672,780

(22) Filed: Sep. 26, 2003

(65) Prior Publication Data

US 2004/0062358 A1 Apr. 1, 2004

Related U.S. Application Data

(62) Division of application No. 09/977,012, filed on Oct. 11, 2001, now Pat. No. 6,690,761
(60) Provisional application No. 60/240,157, filed on Oct. 11, 2000.

(51) Int. Cl.[7] .................................................. A61B 6/14
(52) U.S. Cl. ........................................ 378/169; 378/62
(58) Field of Search ........................... 378/38, 62, 168, 378/169, 170

(56) References Cited

U.S. PATENT DOCUMENTS

| | | | |
|---|---|---|---|
| 3,924,133 A | * 12/1975 | Reiss | 378/62 |
| 4,012,638 A | 3/1977 | Altschuler et al. | |
| 4,251,732 A | 2/1981 | Fried | 250/479 |
| 4,356,400 A | 10/1982 | Polizzi et al. | |
| 4,782,502 A | 11/1988 | Shulz | 378/18 |
| 4,922,915 A | 5/1990 | Arnold | 128/653 R |
| 4,985,906 A | 1/1991 | Arnold | 378/18 |
| 5,001,738 A | 3/1991 | Brooks | 378/170 |
| 5,222,021 A | 6/1993 | Feldman et al. | 364/413.14 |
| 5,235,628 A | 8/1993 | Kalender | 378/207 |
| 5,335,260 A | 8/1994 | Arnold | 378/207 |
| 5,493,601 A | 2/1996 | Fivez et al. | 378/207 |
| 5,562,448 A | * 10/1996 | Mushabac | 433/215 |
| 5,769,072 A | 6/1998 | Olsson et al. | 623/18 |
| 5,852,647 A | 12/1998 | Schick et al. | 378/53 |
| 6,064,716 A | 5/2000 | Siffert et al. | |
| 6,077,224 A | 6/2000 | Lang et al. | 600/437 |
| 6,205,348 B1 | 3/2001 | Giger et al. | 600/407 |
| 6,226,393 B1 | 5/2001 | Grunkin et al. | 382/128 |
| 6,246,745 B1 | 6/2001 | Bi et al. | 378/54 |
| 6,248,063 B1 | 6/2001 | Barnhill et al. | 600/300 |
| 6,302,582 B1 | 10/2001 | Nord et al. | 378/207 |
| 6,320,931 B1 | 11/2001 | Arnold | 378/56 |
| 6,411,729 B1 | 6/2002 | Grunkin | 382/132 |

FOREIGN PATENT DOCUMENTS

| | | |
|---|---|---|
| EP | 0314 506 | 5/1989 |
| EP | 0 678 191 | 10/1995 |
| EP | 1 069 395 | 1/2001 |
| EP | 1 230 896 A2 | 8/2002 |
| GB | 2 023 920 A | 1/1980 |
| WO | WO 99/08597 | 2/1999 |
| WO | WO 99/45845 | 9/1999 |
| WO | WO 99/52331 | 10/1999 |
| WO | WO 02/30283 A2 | 4/2002 |

OTHER PUBLICATIONS

Cann, "Quantitative CT for Determination of Bone Mineral Density: A Review," *Radiology 166*: 509–522 (1988).
Eastell et al., "Treatment of postmenopausal Osteoporosis," *New Engl. J. of Med. 338*:736–746 (1998).
Gluer et al., "Peripheral Measurement Techniques for the Assessment of Osteoporosis," *Semin Nucl. Med.* 27:229–247 (1997).

(List continued on next page.)

*Primary Examiner*—David V Bruce
(74) *Attorney, Agent, or Firm*—Robins & Pasternak LLP

(57) ABSTRACT

The present invention relates to methods and devices for analyzing x-ray images. In particular, devices, methods and algorithms are provided that allow for the accurate and reliable evaluation of bone mineral density and bone structure from x-ray images.

58 Claims, 7 Drawing Sheets

OTHER PUBLICATIONS

Patel et al., "Radiation Dose to the Patient and Operator from a Peripheral Dual X–Ray Absorptiometry System," *Journal of Clinical Densitometry* 2(4):397–401 (1999).

Crawley, E.O., "In Vivo Tissue Characterization Using Quantitative Computed Tomography: A Review," Journal of Medical Engineering & Technology 14(6):233–242, 1990.

Gudmundsdottir, et al., "Veterbral Bone Density in Icelandic Women Using Quantitative Computed Tomography Without an External Reference Phantom," Osteoporosis Int 3:84–89, 1993.

* cited by examiner

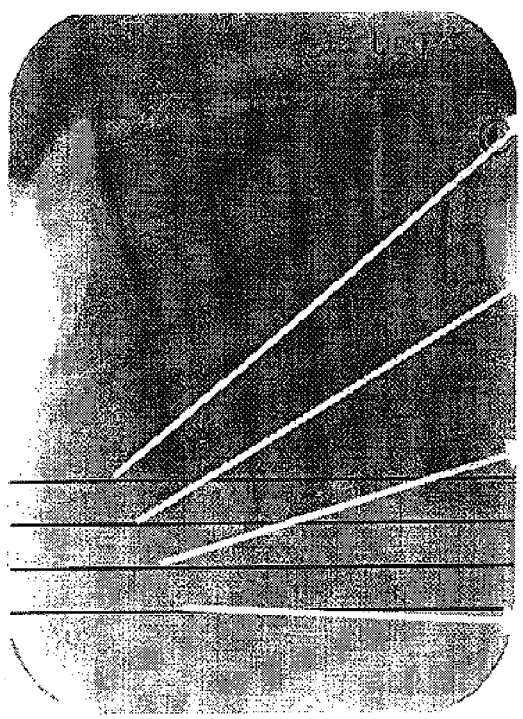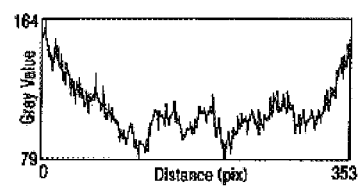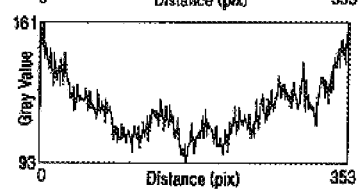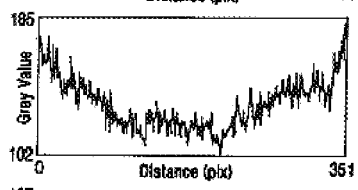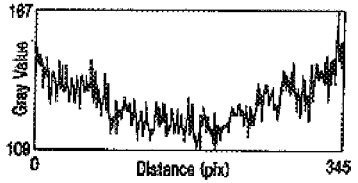
FIG. 6A
FIG. 6B
FIG. 6C
FIG. 6D
FIG. 6E

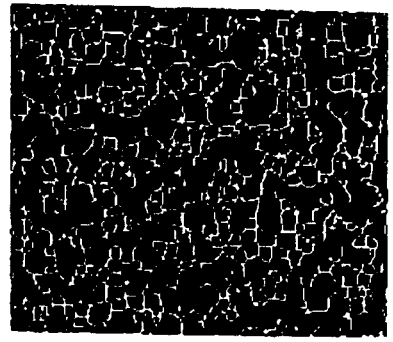
FIG. 7A
FIG. 7B
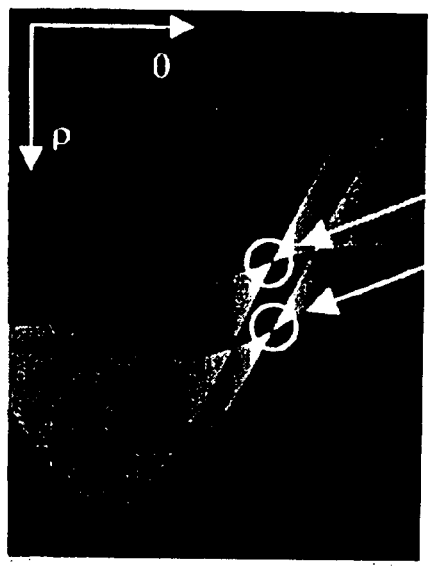
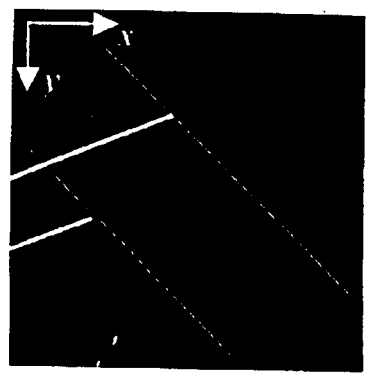
FIG. 8A
FIG. 8B

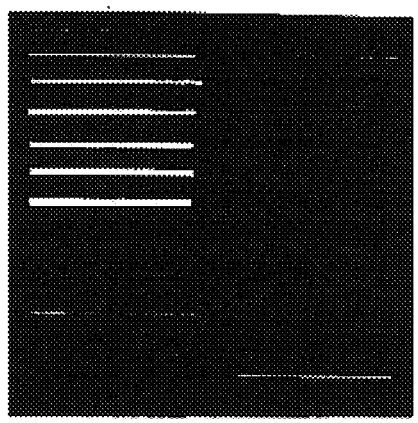
FIG. 9
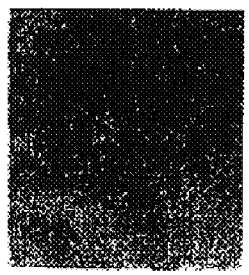
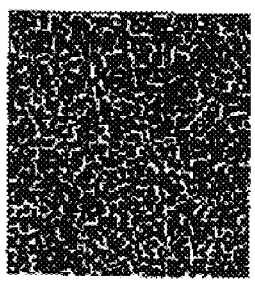
FIG. 10A  FIG. 10B
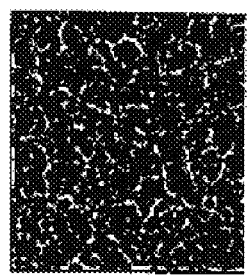
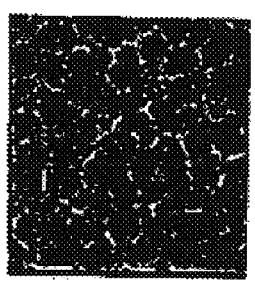
FIG. 10C  FIG. 10D
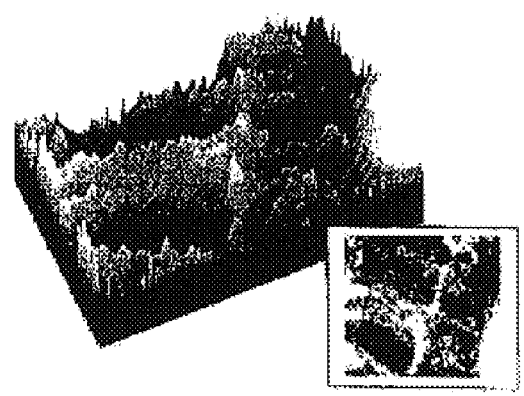
FIG. 11

METHODS AND DEVICES FOR ANALYSIS OF X-RAY IMAGES

CROSS-REFERENCE TO RELATED APPLICATIONS

This application is a divisional of patent application Ser. No. 09/977,012, filed Oct. 11, 2001 now U.S. Pat. No. 6,690,761 and is related to U.S. Provisional Patent Application Ser. No. 60/240,157, filed 11 Oct. 2000, from which priority is claimed under 35 U.S.C. §119(e)(1) and which applications are incorporated herein by reference in their entireties.

TECHNICAL FIELD

The present invention is in the field of x-ray imaging and analysis thereof. In particular, methods and compositions for the accurate analysis of bone mineral density and/or bone structure based on x-rays are described.

BACKGROUND

X-rays and other x-ray image analysis are important diagnostic tools, particularly for bone related conditions. Currently available techniques for the noninvasive assessment of the skeleton for the diagnosis of osteoporosis or the evaluation of an increased risk of fracture include dual x-ray absorptiometry (DXA) (Eastell et al. (1998) *New Engl J. Med* 338:736–746); quantitative computed tomography (QCT) (Cann (1988) *Radiology* 166:509–522); peripheral DXA (pDXA) (Patel et al. (1999) *J Clin Densitom* 2:397–401); peripheral QCT (pQCT) (Gluer et. al. (1997) *Semin Nucl Med* 27:229–247); x-ray image absorptiometry (RA) (Gluer et. al. (1997) *Semin Nucl Med* 27:229–247); and quantitative ultrasound (QUS) (Njeh et al. "Quantitative Ultrasound: Assessment of Osteoporosis and Bone Status" 1999, Martin-Dunitz, London England; U.S. Pat. No. 6,077,224, incorporated herein by reference in its entirety). (See, also, WO 9945845; WO 99/08597; and U.S. Pat. No. 6,246,745).

DXA of the spine and hip has established itself as the most widely used method of measuring BMD. Tothill, P. and D. W. Pye, (1992) *Br J Radiol* 65:807–813. The fundamental principle behind DXA is the measurement of the transmission through the body of x-rays of 2 different photon energy levels. Because of the dependence of the attenuation coefficient on the atomic number and photon energy, measurement of the transmission factors at 2 energy levels enables the area densities (i.e., the mass per unit projected area) of 2 different types of tissue to be inferred. In DXA scans, these are taken to be bone mineral (hydroxyapatite) and soft tissue, respectively. However, it is widely recognized that the accuracy of DXA scans is limited by the variable composition of soft tissue. Because of its higher hydrogen content, the attenuation coefficient of fat is different from that of lean tissue. Differences in the soft tissue composition in the path of the x-ray beam through bone compared with the adjacent soft tissue reference area cause errors in the BMD measurements, according to the results of several studies. Tothill, P. and D. W. Pye, (1992) *Br J Radiol,* 65:807–813; Svendsen, O. L., et al., (1995) *J Bone Min Res* 10:868–873. Moreover, DXA systems are large and expensive, ranging in price between $75,000 and $150,000.

Quantitative computed tomography (QCT) is usually applied to measure the trabecular bone in the vertebral bodies. Cann (1988) *Radiology* 166:509–522. QCT studies are generally performed using a single kV setting (single-energy QCT), when the principal source of error is the variable composition of the bone marrow. However, a dual-kV scan (dual-energy QCT) is also possible. This reduces the accuracy errors but at the price of poorer precision and higher radiation dose. Like DXA, however, QCT are very expensive and the use of such equipment is currently limited to few research centers.

Quantitative ultrasound (QUS) is a technique for measuring the peripheral skeleton. Njeh et al. (1997) *Osteoporosis Int* 7:7–22; Njeh et al. Quantitative Ultrasound: Assessment of Osteoporosis and Bone Status. 1999, London, England: Martin Dunitz. There is a wide variety of equipment available, with most devices using the heel as the measurement site. A sonographic pulse passing through bone is strongly attenuated as the signal is scattered and absorbed by trabeculae. Attenuation increases linearly with frequency, and the slope of the relationship is referred to as broadband ultrasonic attenuation (BUA; units: dB/MHz). BUA is reduced in patients with osteoporosis because there are fewer trabeculae in the calcaneus to attenuate the signal. In addition to BUA, most QUS systems also measure the speed of sound (SOS) in the heel by dividing the distance between the sonographic transducers by the propagation time (units: m/s). SOS values are reduced in patients with osteoporosis because with the loss of mineralized bone, the elastic modulus of the bone is decreased. There remain, however, several limitations to QUS measurements. The success of QUS in predicting fracture risk in younger patients remains uncertain. Another difficulty with QUS measurements is that they are not readily encompassed within the WHO definitions of osteoporosis and osteopenia. Moreover, no intervention thresholds have been developed. Thus, measurements cannot be used for therapeutic decision-making.

There are also several technical limitations to QUS. Many devices use a foot support that positions the patient's heel between fixed transducers. Thus, the measurement site is not readily adapted to different sizes and shapes of the calcaneus, and the exact anatomic site of the measurement varies from patient to patient. It is generally agreed that the relatively poor precision of QUS measurements makes most devices unsuitable for monitoring patients' response to treatment. Gluer (1997) *J Bone Min Res* 12:1280–1288.

Radiographic absorptiometry (RA) is a technique that was developed many years ago for assessing bone density in the hand, but the technique has recently attracted renewed interest. Gluer et al. (1997) *Semin Nucl Med* 27:229–247. With this technique, BMD is measured in the phalanges. The principal disadvantage of RA of the hand is the relative lack of high turn-over trabecular bone. For this reason, RA of the hand has limited sensitivity in detecting osteoporosis and is not very useful for monitoring therapy induced changes.

Peripheral x-ray absorptiometry methods such as those described above are substantially cheaper than DXA and QCT with system prices ranging between $15,000 and $35,000. However, epidemiologic studies have shown that the discriminatory ability of peripheral BMD measurements to predict spine and hip fractures is lower than when spine and hip BMD measurements are used. Cummings et al. (1993) *Lancet* 341:72–75; Marshall et al. (1996) *Br Med J* 312:1254–1259. The main reason for this is the lack of trabecular bone at the measurement sites used with these techniques. In addition, changes in forearm or hand BMD in response to hormone replacement therapy, bisphosphonates, and selective estrogen receptor modulators are relatively small, making such measurements less suitable than measurements of principally trabecular bone for monitoring response to treatment. Faulkner (1998) *J Clin Densitom*

1:279–285; Hoskings et al. (1998) *N Engl J Med* 338:485–492. Although attempts to obtain information on bone mineral density from dental x-rays have been attempted (See, e.g., Shrout et al. (2000) *J. Periodonol.* 71:335–340; Verhoeven et al. (1998) *Clin Oral Implants Res* 9(5):333–342), these have not provided accurate and reliable results.

Furthermore, current methods and devices do not generally take into account bone structure analyses. See, e.g., Ruttimann et al. (1992) *Oral Surg Oral Med Oral Pathol* 74:98–110; Southard & Southard (1992) *Oral Surg Oral Med Oral Pathol* 73:751–9; White & Rudolph, (1999) *Oral Surg Oral Med Oral Pathol Oral Radiol Endod* 88:628–35.

Thus, although a number of devices and methods exist for evaluating bone density, there are a number of limitations on such devices and methods. Consequently, the inventors have recognized the need, among other things, to provide methods and compositions that result in the ability to obtain accurate bone mineral density and bone structure information from dental x-ray images. Additionally, there also remains a need for devices and methods that include dependable and accurate calibration phantoms.

SUMMARY

The present invention meets these and other needs by providing compositions and methods that allow for the analysis of bone mineral density and/or bone structure from x-ray images. In certain embodiments, the x-ray images are dental x-ray images. Also provided are x-ray assemblies comprising accurate calibration phantoms including, in particular, calibration phantoms which act as references in order to determine bone structure from an x-ray image.

In one aspect, the invention includes a method to derive quantitative information on bone structure and/or bone mineral density from a x-ray image comprising (a) obtaining a dental x-ray image, wherein the x-ray image includes (i) at least a portion of the maxilla or mandible and (ii) an external standard for determining bone structure; and (b) analyzing the image obtained in step (a) to derive quantitative information on bone structure. Preferably, the x-ray image a dental x-ray and is obtained on dental x-ray film and the external standard comprises a calibration phantom that projects free of the mandible or maxilla. The calibration phantom can comprise geometric patterns, for example, made of plastic, metal or metal powder.

In certain embodiments, the image is obtained digitally, for example using a selenium detector system or a silicon detector system. In other embodiments, the image can be digitized for analysis.

In any of the methods described herein, the analysis can comprise using one or more computer program (or units). Additionally, the analysis can comprise identifying one or more regions of anatomical interest (ROI) in the image, either prior to, concurrently or after analyzing the image, e.g. for information on bone mineral density and/or bone structure. Bone structural or bone density information at a specified distance from the ROI and/or areas of the image having selected bone structural or bone density information can be identified manually or, preferably, using a computer unit. The region of interest can be, for example, in the mandible, maxilla or one or more teeth. The bone density information can be, for example, areas of highest, lowest or median density. Bone structural information can be, for example, trabecular thickness; trabecular spacing; two-dimensional or three-dimensional spaces between trabecular, two-dimensional or three-dimensional architecture of the trabecular network.

In other aspects, the invention includes a method to derive quantitative information on bone structure from an x-ray image comprising: (a) obtaining an x-ray image; and (b) analyzing the image obtained in step (a) using one or more indices selected from the group consisting of Hough transform, skeleton operator, morphological operators, mean pixel intensity, variance of pixel intensity, fourier spectral analysis, fractal dimension, morphological parameters and combinations thereof, thereby deriving quantitative information on bone structure. The various analysis can be performed concurrently or in series, for example a skeleton operator can be performed before a Hough transform. Further, when using two or more indices they can be weighted differently. Additionally, any of these methods can also include analyzing the image for bone mineral density information using any of the methods described herein.

In another aspect, any of the methods described herein can further comprise applying one or more correction factors to the data obtained from the image. For example, correction factors can be programmed into a computer unit. The computer unit can be the same one that performs the analysis of the image or can be a different unit. In certain embodiments, the correction factors account for the variation in soft-tissue thickness in individual subjects.

In another aspect, any of the methods described herein can further comprise compressing soft tissue in the image to a selected thickness while obtaining the x-ray image.

In yet other aspects, a hygienic cover adapted to receive the external standard is also provided. In other embodiments, the hygienic cover is also adapted to receive x-ray film, for example when dental x-ray film is being used. The hygienic cover can be radiolucent. Additionally, it can be disposable or sterilizable. In certain embodiments, the external standard is integrated into the hygienic cover while in other embodiments the external standard is temporarily attached to the hygienic cover, for example, by insertion into a pocket or compartment, by the use of adhesive or by other mechanical attachment means. Any of the hygienic covers described herein can also include a bolus (e.g., water or saline filled) component. The bolus can be integrated into the hygienic cover or temporarily attached to the hygienic cover, for example, by insertion into a pocket or compartment, by the use of adhesive or by other mechanical attachment means.

In another aspect, the invention comprises a dental x-ray assembly for determining bone mineral density or bone structure comprising (a) a hygienic cover, (b) x-ray film and (c) a calibration phantom comprising at least one marker of known density or structure. The assembly can further comprise a holder, for example for the x-ray film. In cerain embodiments, the hygienic cover is disposable while in other embodiments, the hygienic cover is sterilizable.

In any of the assemblies described herein, the calibration phantom can be integrated into the assembly, for example integrated into the hygienic cover, x-ray film (e.g., between one or two layers of the film) and/or holder. Alternatively, the calibration phantom can be temporarily attached to the assembly, for example by insertion into a compartment of the hygienic cover or by mechanical attachment to the x-ray film. In certain embodiments, the calibration phantom comprises a plurality of geometric patterns (e.g., circles, stars, squares, crescents, ovals, multiple-sided objects, irregularly shaped objects and combinations thereof) that serve as a reference for bone structure characteristics (e.g., trabecular thickness; trabecular spacing; two-dimensional or three-dimensional spaces between trabecular, two-dimensional and/or three-dimensional architecture of the trabecular network). The calibration phantom (or geometric patterns therein) can be made, for example, of metal, plastic, metal powder or combinations thereof. In any of the assemblies described herein, the film can be integral to the hygienic cover. In other embodiments, the calibration phantom is adapted to fit over one or more teeth, for example having the shape of U or a V.

Any of the assemblies described herein can further include a hygienic cover of the assembly can also include a bolus back (e.g., water or saline filled component). The bolus can be integrated into the hygienic cover or temporarily attached to the hygienic cover, for example, by insertion into a pocket or compartment, by the use of adhesive or by other mechanical attachment means.

In yet another aspect, the invention includes a method of accurately determining bone mineral density and/or bone structure of a dental x-ray image, the method comprising: providing any of the assemblies described herein, wherein the calibration phantom is positioned such that x-rays pass through a subject and the calibration phantom simultaneously, wherein the image includes at least a portion of mandible or maxilla; creating an image of the calibration phantom and the mandible or the maxilla; and comparing the image of the calibration phantom and the subject's anatomy to determine bone mineral density and/or bone structure of the subject.

In a still further aspect, the invention includes a kit comprising a hygienic cover, a calibration phantom for bone structure and/or bone density comprising an integrated geometric pattern; a dental x-ray imaging assembly and computer programs, wherein said computer programs analyze and assess bone mineral density and/or bone structure.

In a still further aspect, the invention includes a method of diagnosing a bone condition (e.g., osteoporosis) comprising analyzing an x-ray obtained by any of the methods described herein.

These and other embodiments of the subject invention will readily occur to those of skill in the art in light of the disclosure herein.

BRIEF DESCRIPTION OF THE FIGURES

FIG. 6, panels B through E shows gray value profiles along different rows of pixels used for locating dental apices. From top to bottom, the characteristic peaks for the dental roots (shown in dental x-ray panel A) gradually disappear.

FIG. 7 shows a Hough transform (panel A) of a test image (panel B). All collinear points from the same line are transformed into sinusoidal curves that intersect in a single point (circles).

FIG. 8 shows a Hough transform (panel A) of a skeletonized trabecular bone x-ray image (panel B). The white regions in panel A indicate longer segments and predominant angles.

FIG. 9 shows the effect of varying size of structuring element $E_2$; calibration phantom image with lines of varying width (1, 3, 5, 7, 9, 11, 13 pix) (top left); skeleton operation performed using $E_2$ with a diameter of 3 pix (top right), 7 pix (bottom left), and 11 pix (bottom right), respectively.

FIG. 10 shows the effect of varying size of structuring element $E_2$; gray scale image of trabecular bone (top left, panel A); skeleton operation performed using $E_2$ with a diameter of 3 pix (top right, panel B); 7 pix (bottom left, panel C) and 11 pix (bottom right, panel D), respectively.

FIG. 11 shows gray value surface plot of an anatomical region of interest from a dental x-ray (inset) used for fractal analysis.

DETAILED DESCRIPTION

Figure 1:
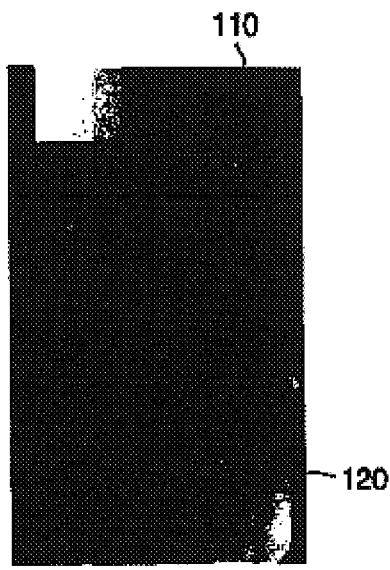
FIG. 1 shows an example of a dental x-ray. A calibration phantom 110 is seen. Regions of interest 120 have been placed for measurement of bone mineral density or structure.
Figure 2:
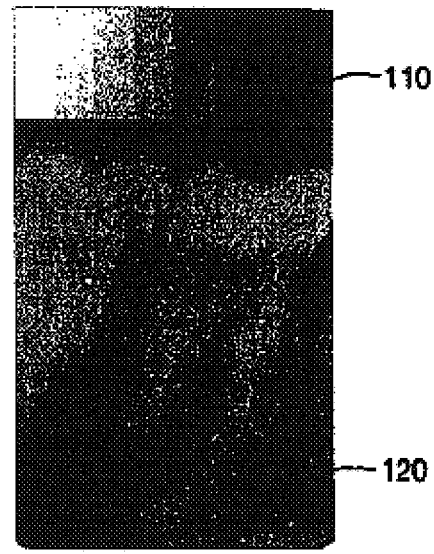
FIG. 2 shows another example of a dental x-ray. A calibration phantom 110 is seen. Regions of interest 120 have been placed for measurement of bone mineral density or structure.
Figure 3:
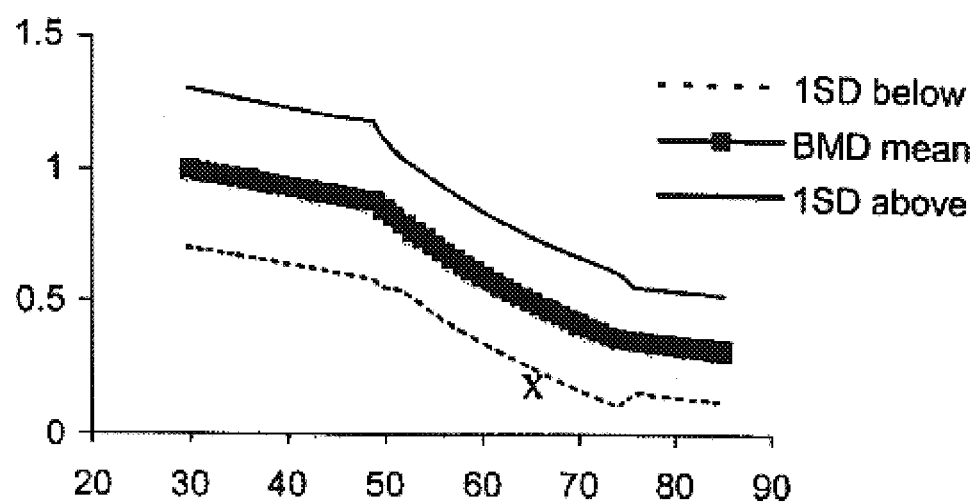
FIG. 3 shows an example of an analysis report resulting from a measurement of mandibular or maxillary bone mineral density. A subject (X) is more than one standard deviation below the mean of age-matched controls (x-axis age, y-axis arbitrary units BMD).

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The practice of the present invention employs, unless otherwise indicated, conventional methods of x-ray imaging and processing within the skill of the art. Such techniques are explained fully in the literature. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to "a calibration phantom" includes a one or more such phantoms.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "dental x-ray" refers to any x-ray that includes at least a portion of the mandible and/or maxilla The x-ray may include portions or the whole of both mandible and maxilla. Similarly, teeth may or may not be included. Thus, dental x-rays refer to images of mandible and/or maxilla even in adentulous subjects.

"Osteoporosis" refers to a condition characterized by low bone mass and microarchitectural deterioration of bone tissue, with a consequent increase of bone fragility and susceptibility to fracture. Osteoporosis presents most commonly with vertebral fractures due to the decrease in bone mineral density and deterioration of structural properties of bone.

A "subject" preferably refers to an animal, for example a mammal such as a human. As used herein the term "patient" refers to a human subject.

"Computational unit" refers to any current or future software, chip or other device used for calculations, such as bone structure, now developed or developed in the future. The computational unit may be designed to determine the shortest reflective distance when two or more ultrasound sources are employed at different transmission angles. The computational unit may be designed to control the x-ray assembly or detector (as well as other parameters related to the x-ray detector). Other applications of the computational unit to the methods and devices described herein will be recognized by those skilled in the art. The computational unit may be used for any other application related to this technology that may be facilitated with use of computer software or hardware.

General Overview

Methods and compositions useful in analyzing x-ray images are described. In particular, the invention includes methods of obtaining and/or deriving information about bone mineral density and/or bone structure from an x-ray image. Additionally, the present invention relates to the provision of accurate calibration phantoms for use in determining bone structure and methods of using these calibration phantoms. In particular, the present invention recognizes for the first time that errors arising from misplacement of interrogation sites in dental x-rays of bone density and structure can be corrected by positioning the detector and/or calibration reference with respect to an anatomical landmark (or anatomical region of interest).

Advantages of the present invention include, but are not limited to, (i) providing accessible and reliable means for analyzing x-rays; (ii) providing accurate calibration phantoms for determining bone structure and/or bone density, (iii) providing accurate calibration phantoms that can be readily used with standard dental x-ray technology; (iv) providing disposable or sterilizable hygienic covers adapted to receive one or more calibration phantoms and, optionally, one or more fluid-filled bolus backs; (v) providing algorithms and devices that enhance accuracy of the information obtained from an x-ray, for example by correcting for variations in soft tissue thickness; and (vi) providing algorithms and methods for predicting and/or treating bone-related disorders.

1.0. Obtaining Data from Dental X-Rays

An x-ray image can be acquired using well-known techniques from any local site. For example, in certain aspects, 2D planar x-ray imaging techniques are used. 2D planar x-ray imaging is a method that generates an image by transmitting an x-ray beam through a body or structure or material and by measuring the x-ray attenuation on the other side of said body or said structure or said material. 2D planar x-ray imaging is distinguishable from cross-sectional imaging techniques such as computed tomography or magnetic resonance imaging. If the x-ray image was captured using conventional x-ray film, the x-ray can be digitized using any suitable scanning device. Digitized x-ray images can be transmitted over a networked system, e.g. the Internet, into a remote computer or server. It will be readily apparent that x-ray images can also be acquired using digital acquisition techniques, e.g. using phosphorus plate systems or selenium or silicon detector systems, the x-ray image information is already available in digital format which can be easily transmitted over a network.

Dental x-rays are preferred because of the relative ease and lack of expense in obtaining these images. Further, the mandible and maxilla are primarily trabecular bone. Since the metabolic turnover of trabecular bone is approximately eight times greater than that of cortical bone, areas of predominantly trabecular bone such as the vertebral body are preferred sites for measuring bone mineral density. Lang et al. (1991) *Radiol Clin North Am* 29:49–76. Thus, the fact that trabecular bone is clearly visible on the dental x-ray image, thus lending itself to quantitative analysis of bone mineral density and structure. Jeffcoat et al. (2000) *Periodontol* 23:94–102; Southard et al. (2000) *J Dent Res* 79:964–969. Further, the earliest bone loss in osteoporosis patients occurs in areas of trabecular bone. Multiple dental x-ray images are commonly made in most Americans throughout life. Indeed, there are approximately 750 million U.S. dental visits annually and 150 million of these patients result in more than 1 billion dental x-rays taken each year. Thus, the ability to diagnose osteoporosis on dental x-rays would be extremely valuable since it would create the opportunity for low-cost mass screening of the population.

Preferably, x-ray imaging is performed using standard dental x-ray equipment (General Electric Medical Systems, Milwaukee, Wis.). X-rays of the incisor region and canine region is acquired using a standard x-ray imaging technique with 80 kVp and automatic exposure using a phototimer or using a manual technique with 10 mA tube current. X-ray images are acquired on Kodak Ultraspeed film (Kodak, Rochester, N.Y.). X-ray images may be digitized using a commercial flatbed scanner with transparency option (Acer ScanPremio ST).

1.1. Calibration Phantoms

It is highly preferred that the x-ray images include accurate reference markers, for example calibration phantoms for assessing bone mineral density and/or bone structure of any given x-ray image. Calibration references (also known as calibration phantoms) for use in imaging technologies have been described. See, e.g., U.S. Pat. No. 5,493,601 and U.S. Pat. No. 5,235,628. U.S. Pat. No. 5,335,260 discloses a calibration phantom representative of human tissue containing variable concentrations of calcium that serves as reference for quantifying calcium, bone mass and bone mineral density in x-ray and CT imaging systems. However, currently available calibration phantoms are not always accurate, particularly in cases where bone structure is being analyzed. Because bone mineral density accounts for considerably less than 100% of fracture risk in osteoporosis (Ouyang et al. (1997) *Calif Tissue Int*, 60:139–147) some of the methods and devices described herein are designed to assess not only bone mineral density but also bone structure.

By assessing both these parameters, more accurate testing and screening can be provided for conditions such as osteoporosis.

Thus, in certain aspects, the current invention provides for methods and devices that allow accurate quantitative assessment of information contained in an x-ray such as density of an anatomic structure and/or morphology of an anatomic structure. Any suitable calibration phantom can be used, for example, one that comprises aluminum or other radio-opaque materials. U.S. Pat. No. 5,335,260 describes other calibration phantoms suitable for use in assessing bone mineral density in x-ray images. Examples of other suitable calibration reference materials can be fluid or fluid-like materials, for example, one or more chambers filled with varying concentrations of calcium chloride or the like.

Numerous calibration phantoms (or reference calibrations) can be used in the practice of the present invention. Typically, the system used to monitor bone mineral density and/or bone structure in a target organism comprises a dental x-ray, which provides information on the subject; an assembly including a calibration phantom, which acts as a reference for the data in the dental x-ray; and at least one data processing system, which evaluates and processes the data from the dental x-ray image and/or from the calibration phantom assembly.

Figure 4:
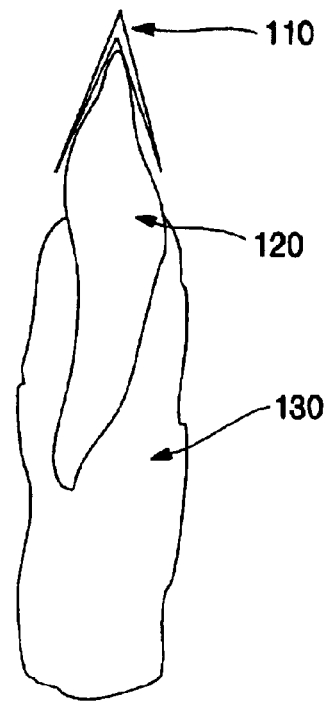
FIG. 4 shows an example of a V-shaped calibration phantom 110 mounted on a tooth 120. Gums are also shown 130.

It will be readily apparent that a calibration phantom can contain a single, known density or structure reference. Furthermore, a gradient in x-ray density can be achieved by varying the thickness or the geometry of the calibration phantom along the path of the x-ray beam, for example, by using a V-shape of the calibration phantom of varying thickness (FIG. 4).

The calibration phantom can contain several different areas of different radio-opacity. For example, the calibration phantom can have a step-like design, whereby changes in local thickness of the wedge result in differences in radio-opacity. Stepwedges using material of varying thickness are frequently used in radiology for quality control testing of x-ray beam properties. By varying the thickness of the steps, the intensity and spectral content of the x-ray beam in the projection image can be varied. Stepwedges are commonly made of aluminum, copper and other convenient and homogeneous materials of known x-ray attenuation properties. Stepwedge-like phantoms can also contain calcium phosphate powder or calcium phosphate powder in molten paraffin.

Alternatively, the calibration reference may be designed such that the change in radio-opacity is from periphery to center (for example in a round, ellipsoid, rectangular of other shaped structure). As noted above, the calibration reference can also be constructed as plurality of separate chambers, for example fluid filled chambers, each including a specific concentration of a reference fluid (e.g., calcium chloride).

In certain embodiments, the calibration phantom is specifically designed to serve as a reference for bone structure (e.g., trabecular spacing, thickness and the like). For example, the calibration wedge can contain one or more geometric patterns with known dimensions, e.g. a grid whereby the spacing of a grid, thickness of individual grid elements, etc. are known. This known geometric pattern of radio-opaque elements in the calibration phantom can be used to improve the accuracy of measurements of trabecular bone structure in an x-ray. Such measurements of trabecular bone structure can include, but are not limited to, trabecular spacing, trabecular length and trabecular thickness. Such measurements of trabecular spacing, trabecular length and trabecular thickness can, for example, be performed in a dental x-ray. These calibration phantoms can be made up of a variety of materials include, plastics, metals and combinations thereof. Further, the reference components can be solid, powdered, fluid or combinations thereof. Thus, the calibration wedge can also be used to improve measurements of bone structure.

Since the present invention contemplates, e.g., analysis of dental x-ray images for information on bone structure, bone mineral density or both structure and density, it will be apparent that calibration phantoms will be selected based on whether structure, density or both are being measured. Thus, one or more calibration phantoms may be present.

Whatever the overall shape or composition of the calibration phantom, when present, the at least one marker be positioned at a known density and/or structure in the phantom. Furthermore, it is preferred that at least one geometric shape or pattern is included in the calibration phantom. Any shape can be used including, but not limited to, squares, circles, ovals, rectangles, stars, crescents, multiple-sided objects (e.g., octagons), V- or U-shaped, inverted V- or U-shaped, irregular shapes or the like, so long as their position is known to correlate with a particular density of the calibration phantom. In preferred embodiments, the calibration phantoms described herein are used in 2D planar x-ray imaging.

The calibration phantoms can be imaged before or after the x-ray image is taken. Alternatively, the calibration phantom can be imaged at the same time as the x-ray image. The calibration phantom can be physically connected to an x-ray film and/or film holder. Such physical connection can be achieved using any suitable mechanical or other attachment mechanism, including but not limited to adhesive, a chemical bond, use of screws or nails, welding, a Velcro™ strap or Velcro™ material and the like. Similarly, a calibration phantom can be physically connected to a detector system or a storage plate for digital x-ray imaging using one or more attachment mechanisms (e.g., a mechanical connection device, a Velcro™ strap or other Velcro™ material, a chemical bond, use of screws or nails, welding and an adhesive).

Additionally, the calibration phantom assembly can be attached to an anatomical structure, for example one or more teeth, mucus membranes, the mandible and/or maxilla For instance, the calibration phantom can be attached (e.g., via adhesive attachment means) to the epithelium or mucous membrane inside overlying the mandible or the maxilla. Alternatively, the calibration phantom can be placed on or adjacent to a tooth, for example, a V- or U-shaped (in the case of the maxilla) or an inverted V- or U-shaped (in the case of the mandible) calibration phantom can be used. The opening of the V or U will be in contact with the free edge of at least one tooth or possibly several teeth (FIG. 4).

It will be apparent that calibration phantoms suitable for attachment to an anatomical structure can have different shapes depending on the shape of the anatomical structure (e.g., tooth or teeth) on which or adjacent to which it will be placed including, but not limited to, U-shaped, V-shaped, curved, flat or combinations thereof. For example, U-shaped (or inverted U-shaped) calibration phantoms can be positioned on top of molars while V-shaped (or inverted V-shaped) calibration phantoms can be positioned on top of incisors. Further, it will be apparent that in cerain instances (e.g., teeth on the mandible), the calibration phantom can rest on top of the tooth just based on its gravity or it can be attached to the tooth (e.g., using adhesive). In the case of the teeth on the maxilla, the calibration phantom will typically be attached to the tooth, for example with use of an adhesive.

Any of these attachments may be permanent or temporary and the calibration phantom can be integral (e.g., built-in) to the film, film holder and/or detector system or can be attached or positioned permanently or temporarily appropriately after the film and/or film holder is produced. Thus, the calibration phantom can be designed for single-use (e.g., disposable) or for multiple uses with different x-ray images. Thus, in certain embodiments, the calibration phantom is reusable and, additionally, can be sterilized between uses. Integration of a calibration phantom can be achieved by including a material of known x-ray density between two of the physical layers of the x-ray film. Integration can also be achieved by including a material of known x-ray density within one of the physical layers of the x-ray film. Additionally, the calibration phantom can be integrated into the film cover. A calibration phantom or an external standard can also be integrated into a detector system or a storage plate for digital x-ray imaging. For example, integration can be achieved by including a material of known x-ray density between two of the physical layers of the detector system or the storage plate. Integration can also be achieved by including a material of know x-ray density within one of the physical layers of the detector system or the storage plate.

In certain embodiments, for example those embodiments in which the calibration phantom is temporarily attached to a component of the x-ray assembly system (e.g., x-ray film holder, x-ray film, detector system or the like), cross-hairs, lines or other markers may be placed on the apparatus as indicators for positioning of the calibration phantom. These indicators can help to ensure that the calibration phantom is positioned such that it doesn't project on materials that will alter the apparent density in the resulting image.

Any of the calibration phantom-containing assemblies described herein can be used in methods of analyzing and/or quantifying bone structure (or bone mineral density) in an x-ray image. The methods generally involve simultaneously imaging or scanning the calibration phantom and another material (e.g., bone tissue from a subject) for the purpose of quantifying the density of the imaged material (e.g., bone mass). The calibration phantom, the x-ray tube or dental x-ray film is typically positioned in a manner to ensure inclusion of the calibration phantom and a portion of the mandible and/or maxilla on the dental x-ray image. Preferably, the calibration phantom, the x-ray tube and the dental x-ray film are positioned so that at least a portion of the section of the mandible or maxilla included on the image will contain predominantly trabecular bone rather than cortical bone.

Thus, under the method of the present invention, the calibration phantom is preferably imaged or scanned simultaneously with the individual subject, although the invention allows for non-simultaneous scanning of the phantom and the subject. Methods of scanning and imaging structures by x-ray imaging technique are well known. By placing the calibration phantom in the x-ray beam with the subject, reference calibration samples allow corrections and calibration of the absorption properties of bone. When the phantom is imaged or scanned simultaneously with each subject, the variation in x-ray beam energy and beam hardening are corrected since the phantom and the subject both see the same x-ray beam spectrum. Each subject, having a different size, thickness, muscle-to-fat ratio, and bone content, attenuate the beam differently and thus change the effective x-ray beam spectrum. It is necessary that the bone-equivalent calibration phantom be present in the same beam spectrum as the subject's bone to allow accurate calibration.

X-ray imaging assemblies that are currently in use do not take into account the position of the calibration phantom in relation to the structures being imaged. Thus, when included in known assemblies, calibration phantom(s) are often positioned such that they project on materials or structures (e.g., bone) that alter apparent density of the calibration phantom in the resulting x-ray image. Clearly, this alteration in apparent density will affect the accuracy of the calibration phantom as a reference for determining bone mineral density. Therefore, it is an object of the invention to provide methods in which the calibration phantom projects free of materials or structures that will alter the apparent density of the reference. In the context of dental x-rays, for instance, the methods described herein ensure that the calibration phantom projects free of bone (e.g., teeth, jaw) tissue. This can be accomplished in a variety of ways, for example, positioning the calibration phantom in the x-ray film or in the x-ray film holder such that it will appear between the teeth in the dental x-ray.

The calibration phantom materials and methods of the present invention are preferably configured to be small enough and thin enough to be placed inside the mouth, and the method of the present invention can be used to quantify bone mass using standard dental x-ray systems, for example by including temporary or permanent calibration phantoms in dental x-ray film holders. Further, it is highly desirable that the calibration phantom be positioned so that at least a portion doesn't project on structures or materials that will alter the apparent density or structural characteristics of the calibration phantoms. It is also preferable to position calibration phantom at a defined distance relative to at least one tooth or the mandible or the maxilla whereby a substantial portion of the calibration phantom projects free of said tooth, said mandible or said maxilla on the x-ray image. Any suitable distance can be used, for example between about 1 mm and 5 cm or any value therebetween.

1.2. Inherent Reference Markers

In certain embodiments of the invention, information inherent in the anatomic structure or the non-living object can be used to estimate the density and/or structure of selected bone regions of interest within the anatomic structure or the non-living object. For example, since the x-ray density of muscle, fat, and air are known, the density of air surrounding an anatomic structure or non-living object, the density of subcutaneous fat, and the density of muscle tissue can be used to estimate the density of a selected region of bone, for example within the distal radius.

The information inherent in said anatomic structure can also be combined with information provided by the calibration phantom and the combination can result in an improved accuracy of the calibration phantom.

1.3. Holders and Hygienic Covers

Figure 5:
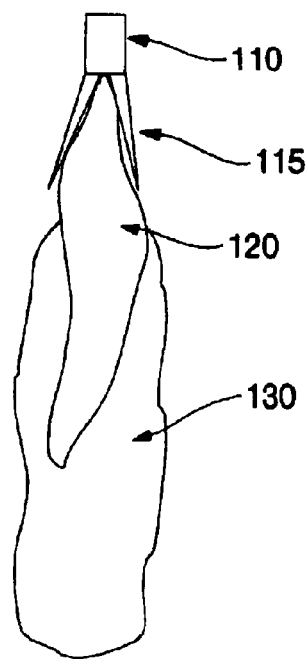
FIG. 5 shows an example of a holder 115 for a calibration phantom 110. The holder 115 is mounted on a tooth 120. Gums are also shown 130.

As noted above, in certain embodiments, a holder can be used to position the calibration phantom. The holder can be U-shaped or V-shaped (FIG. 5) for ease in attachment to a tooth. The attachment can be, for example, with an adhesive. The calibration phantom, in turn, can be attached to the holder. Similarly, the calibration phantom can be attached to holders comprising one or more molds of at least one or more teeth. Additionally, the holder can be used to position both the film and the calibration phantom relative to the osseous structure that will be included in the x-ray image. In another embodiment, a holding device that can hold the x-ay film is integrated in the calibration phantom. This holding device can hold the film in place prior to taking the x-ray. The holding device can be spring-loaded or use other means such as mechanical means of holding and stabilizing the x-ray film.

In certain embodiments, the holder may comprise a disposable or sterilizeable hygienic cover. See, e.g., WO 99/08598, the disclosure of which is incorporated by reference herein in its entirety. Furthermore, the holder may comprise multiple components, for example, the calibration phantom and a integrated or insertable bolus back that can serve to enhance the accuracy of the calibration phantom by accounting for the effect of soft tissue that may project with the calibration phantom and/or with the bone.

In certain embodiments, the calibration phantom can be configured so that it stabilizes against the surrounding tissues on its own without the use of an additional holder. The calibration phantom can be protected with a hygienic cover.

The holder (e.g. hygienic cover) may be comprised of a rigid material, a flexible material or combinations thereof. Furthermore, the holder may include one or more pockets/compartments adapted to receive additional components such as the calibration phantom, a bolus back or the like. Additionally, one or more portions of the holder may be radiolucent.

2.0. Analysis and Manipulation of Data

The data obtained from x-ray images taken as described above is then preferably analyzed and manipulated. Thus, the systems and assemblies described herein can also include one or more computational units designed, for example, to analyze bone density or bone structure data in the image; to identify an anatomical landmark in an anatomical region; to correct for soft tissue measurements; and/or to evaluate bone density and structure of the image. The computational unit can also further comprise a database comprising reference anatomical maps and the computational unit is further designed to compare the anatomical map with the reference anatomical map. The reference anatomical map may be historic (from the same or another patient, generated as part of an interrogation protocol), or theoretical or any other type of desired reference map.

Any x-ray image can be analyzed in order to obtain and manipulate data. Thus, data points, derived data, and data attributes database according to the present invention may comprise the following: (1) the collection of data points, said data points comprising information obtained from an x-ray image, for example, bone mineral density information or information on bone structure (architecture); and (2) the association of those data points with relevant data point attributes. The method may further comprise (3) determining derived data points from one or more direct data points and (4) associating those data points with relevant data point attributes. The method may also comprise (5) collection of data points using a remote computer whereby said remote computer operates in a network environment.

In certain preferred embodiments, the information is obtained from a dental x-ray image. As described herein, dental x-ray images can be acquired at a local site using known techniques. If the x-ray image was captured using conventional x-ray film, the data points (information) of the x-ray image can be digitized using a scanning device. The digitized x-ray image information can then be transmitted over the network, e.g. the Internet, into a remote computer or server. If the x-ray image was acquired using digital acquisition techniques, e.g. using phosphorus plate systems or selenium or silicon detector systems, the x-ray image information is already available in digital format. In this case the image can be transmitted directly over the network, e.g. the Internet. The information can also be compressed and/or encrypted prior to transmission. Transmission can also be by other methods such as fax, mail or the like.

2.1. Data Points

Thus, the methods of formulating data points, derived data, and data attributes database that forms an aspect of the present invention begins with the collection of data sets of measurement values, for example measurements of bone mineral density or bone structure (architecture), for example from dental x-ray images of the mandible or maxilla. Records may be formulated in spreadsheet-like format, for example including data attributes such as date of x-ray, patient age, sex, weight, current medications, geographic location, etc. The database formulation method of the present invention may further comprise the calculation of derived or calculated data points from one or more acquired data points. A variety of derived data points may be useful in providing information about individuals or groups during subsequent database manipulation, and are therefore typically included during database formulation. Derived data points include, but are not limited to the following: (1) maximum bone mineral density, determined for a selected region of bone or in multiple samples from the same or different subjects; (2) minimum bone mineral density, determined for a selected region of bone or in multiple samples from the same or different subjects; (3) mean bone mineral density, determined for a selected region of bone or in multiple samples from the same or different subjects; (4) the number of measurements that are abnormally high or low, determined by comparing a given measurement data point with a selected value; and the like. Other derived data points will be apparent to persons of ordinary skill in the art in light of the teachings of the present specification. The amount of available data and data derived from (or arrived at through analysis of) the original data provide provides an unprecedented amount of information that is very relevant to management of bone related diseases such as osteoporosis. For example, by examining subjects over time, the efficacy of medications can be assessed.

Measurements and derived data points are collected and calculated, respectively, and may be associated with one or more data attributes to form a database.

Data attributes can be automatically input with the x-ray image and can include, for example, chronological information (e.g., DATE and TIME). Other such attributes may include, but are not limited to, the type of x-ray imager used, scanning information, digitizing information and the like. Alternatively, data attributes can be input by the subject and/or operator, for example subject identifiers, i.e. characteristics associated with a particular subject. These identifiers include but are not limited to the following: (1) a subject code (e.g., a numeric or alpha-numeric sequence); (2) demographic information such as race, gender and age; (3) physical characteristics such as weight, height and body mass index (BMI); (4) selected aspects of the subject's medical history (e.g., disease states or conditions, etc.); and (5) disease-associated characteristics such as the type of bone disorder, if any; the type of medication used by the subject. In the practice of the present invention, each data point would typically be identified with the particular subject, as well as the demographic, etc. characteristic of that subject.

Other data attributes will be apparent to persons of ordinary skill in the art in light of the teachings of the present specification.

2.2. Storage of Data Sets and Association of Data Points with Relevant Data Attributes A number of formats exist for storing data sets and simultaneously associating related attributes, including but not limited to (1) tabular, (2) relational, and (3) dimensional. In general the databases comprise data points, a numeric value which correspond to physical measurement (an "acquired" datum or data point) or to a single numeric result calculated or derived from one or more acquired data points that are obtained using the various methods disclosed herein. The databases can include raw data or can also include additional related information, for example data tags also referred to as "attributes" of a data point. The databases can take a number of different forms or be structured in a variety of ways.

The most familiar format is tabular, commonly referred to as a spreadsheet. A variety of spreadsheet programs are currently in existence, and are typically employed in the practice of the present invention, including but not limited to Microsoft Excel spreadsheet software and Corel Quattro spreadsheet software. In this format, association of data points with related attributes occurs by entering a data point and attributes related to that data point in a unique row at the time the measurement occurs.

Further, rational, relational (Database Design for Mere Mortals, by Michael J. Hernandez, 1997, Addison-Wesley Pub. Co., publisher, Database Design for Smarties, by Robert J. Muller, 1999, Morgan Kaufmann Publishers, publisher, Relational Database Design Clearly Explained, by Jan L. Harrington, 1998, Morgan Kaufmann Publishers, publisher) and dimensional (Data-Parallel Computing, by V. B. Muchnick, et al., 1996, International Thomson Publishing, publisher, Understanding Fourth Dimensions, by David Graves, 1993, Computerized Pricing Systems, publisher) database systems and management may be employed as well.

Relational databases typically support a set of operations defined by relational algebra. Such databases typically include tables composed of columns and rows for the data included in the database. Each table of the database has a primary key, which can be any column or set of columns, the values for which uniquely identify the rows in a table. The tables in the database can also include a foreign key that is a column or set of columns, the values of which match the primary key values of another table. Typically, relational databases also support a set of operations (e.g., select, join and combine) that form the basis of the relational algebra governing relations within the database.

Such relational databases can be implemented in various ways. For instance, in Sybase® (Sybase Systems, Emeryville, Calif.) databases, the tables can be physically segregated into different databases. With Oracle® (Oracle Inc., Redwood Shores, Calif.) databases, in contrast, the various tables are not physically separated, because there is one instance of work space with different ownership specified for different tables. In some configurations, databases are all located in a single database (e.g., a data warehouse) on a single computer. In other instances, various databases are split between different computers.

It should be understood, of course, that the databases are not limited to the foregoing arrangements or structures. A variety of other arrangements will be apparent to those of skill in the art.

2.3. Data Manipulation

Data obtained from x-ray images as described herein can be manipulated, for example, using a variety of statistical analyses, to produce useful information. The databases of the present invention may be generated, for example, from data collected for an individual or from a selected group of individuals over a defined period of time (e.g., days, months or years), from derived data, and from data attributes.

For example, data may be aggregated, sorted, selected, sifted, clustered and segregated by means of the attributes associated with the data points. A number of data mining software programs exist which may be used to perform the desired manipulations.

Relationships in various data can be directly queried and/or the data analyzed by statistical methods to evaluate the information obtained from manipulating the database.

For example, a distribution curve can be established for a selected data set, and the mean, median and mode calculated therefor. Further, data spread characteristics, e.g. variability, quartiles and standard deviations can be calculated.

The nature of the relationship between any variables of interest can be examined by calculating correlation coefficients. Useful methods for doing so include but are not limited to the following: Pearson Product Moment Correlation and Spearman Rank Order Correlation.

Analysis of variance permits testing of differences among sample groups to determine whether a selected variable has a discernible effect on the parameter being measured.

Non-parametric tests may be used as a means of testing whether variations between empirical data and experimental expectancies are attributable merely to chance or to the variable or variables being examined. These include the Chi Square test, the Chi Square Goodness of Fit, the 2×2 Contingency Table, the Sign Test, and the Phi Correlation Coefficient.

There are numerous tools and analyses available in standard data mining software that can be applied to the analysis of the databases of the present invention. Such tools and analyses include, but are not limited to, cluster analysis, factor analysis, decision trees, neural networks, rule induction, data driven modeling, and data visualization. Some of the more complex methods of data mining techniques are used to discover relationships that are more empirical and data-driven, as opposed to theory-driven, relationships.

Exemplary data mining software that can be used in analysis and/or generation of the databases of the present invention includes, but is not limited to: Link Analysis (e.g., Associations analysis, Sequential Patterns, Sequential time patterns and Bayes Networks); Classification (e.g., Neural Networks Classification, Bayesian Classification, k-nearest neighbors classification, linear discriminant analysis, Memory based Reasoning, and Classification by Associations); Clustering (e.g., k-Means Clustering, demographic clustering, relational analysis, and Neural Networks Clustering); Statistical methods (e.g., Means, Std dev, Frequencies, Linear Regression, non-linear regression, t-tests, F-test, Chi2 tests, Principal Component Analysis, and Factor Analysis); Prediction (e.g., Neural Networks Prediction Models, Radial Based Functions predictions, Fuzzy logic predictions, Times Series Analysis, and Memory based Reasoning); Operating Systems, and Others (e.g., Parallel Scalability, Simple Query Language functions, and C++objects generated for applications). Companies that provide such software include, for example, the following: Adaptative Methods Group at UTS (UTS City Campus, Sydney, NSW 2000), CSI®, Inc., (Computer Science Innovations, Inc. Melbourne, Fla.), IBM® (International Business Machines Corporation, Armonk, N.Y.), Oracle® (Oracle Inc., Redwood Shores, Calif.) and SAS® (SAS Institute Inc., Cary, N.C.).

These methods and processes may be applied to the data obtained using the methods described herein, for example, databases comprising, x-ray image data sets, derived data, and data attributes.

For a general discussion of statistical methods applied to data analysis, see Applied Statistics for Science and Industry, by A. Romano, 1977, Allyn and Bacon, publisher.

The data is preferably stored and manipulated using one or more computer programs or computer systems. These systems will typically have data storage capability (e.g., disk drives, tape storage, CD-ROMs, etc.). Further, the computer systems may be networked or may be stand-alone systems. If networked, the computer system would be able to transfer data to any device connected to the networked computer system for example a medical doctor or medical care facility using standard e-mail software, a central database using database query and update software (e.g., a data warehouse of data points, derived data, and data attributes obtained from a large number of subjects). Alternatively, a user could access from a doctors office or medical facility, using any computer system with Internet access, to review historical data that may be useful for determining treatment.

If the networked computer system includes a World Wide Web application, the application includes the executable code required to generate database language statements, for example, SQL statements. Such executables typically include embedded SQL statements. The application further includes a configuration file that contains pointers and addresses to the various software entities that are located on the database server in addition to the different external and internal databases that are accessed in response to a user request. The configuration file also directs requests for database server resources to the appropriate hardware, as may be necessary if the database server is distributed over two or more different computers.

Usually each networked computer system includes a World Wide Web browser that provides a user interface to the networked database server. The networked computer system is able to construct search requests for retrieving information from a database via a Web browser. With access to a Web browser users can typically point and click to user interface elements such as buttons, pull down menus, and other graphical user interface elements to prepare and submit a query that extracts the relevant information from the database. Requests formulated in this manner are subsequently transmitted to the Web application that formats the requests to produce a query that can be used to extract the relevant information from the database.

When Web-based applications are utilized, the Web application accesses data from a database by constructing a query in a database language such as Sybase or Oracle SQL which is then transferred to a relational database management system that in turn processes the query to obtain the pertinent information from the database.

Accordingly, in one aspect the present invention describes a method of providing data obtained from x-ray images on a network, for example the Internet, and methods of using this connection to provide real-time and delayed data analysis. The central network can also allow access by the physician to a subject's data. Similarly, an alert could be sent to the physician if a subject's readings are out of a predetermined range, etc. The physician can then send advice back to the patient via e-mail or a message on a web page interface. Further, access to the entire database of data from all subjects may be useful to the for statistical or research purposes. Appropriate network security features (e.g., for data transfer, inquiries, device updates, etc.) are of course employed.

Further, a remote computer can be used to analyze the x-ray that has been transmitted over the network automatically. For example, x-ray density information or structural information about an object can be generated in this fashion. X-ray density information can, for example, be bone mineral density. If used in this fashion, the test can be used to diagnose bone-related conditions such as osteoporosis.

2.4. Graphical User Interface

In certain of the computer systems, an interface such as an interface screen that includes a suite of functions is included to enable users to easily access the information they seek from the methods and databases of the invention. Such interfaces usually include a main menu page from which a user can initiate a variety of different types of analyses. For example, the main menu page for the databases generally include buttons for accessing certain types of information, including, but not limited to, project information, inter-project comparisons, times of day, events, dates, times, ranges of values, etc.

2.5. Computer Program Products

A variety of computer program products can be utilized for conducting the various methods and analyses disclosed herein. In general, the computer program products comprise a computer-readable medium and the code necessary to perform the methods set forth supra. The computer-readable medium on which the program instructions are encoded can be any of a variety of known medium types, including, but not limited to, microprocessors, floppy disks, hard drives, ZIP drives, WORM drives, magnetic tape and optical medium such as CD-ROMs.

For example, once an x-ray image or data from that image is transmitted via a local or long-distance computer network and the data on the x-ray received by a remote computer or a computer connected to the remote network computer, an analysis of the morphology and density of the bone can be performed, for example using suitable computer programs. This analysis of the object's morphology can occur in two-dimensions, although it is also possible in three-dimensions, in particular when x-ray images have been acquired through the anatomic object using multiple different x-ray transmission angles. For example, in imaging osseous structures, such morphological analysis of the transmitted x-ray image can be used to measure parameters that are indicative or suggestive of bone loss or metabolic bone disease. Such parameters include all current and future parameters that can be used to evaluate osseous structures. For example, such parameters include, but are not limited to, trabecular spacing, trabecular thickness and intertrabecular space.

Information on the morphology or 2D or 3D morphology of an anatomic structure can be derived more accurately, when x-ray image acquisition parameters such as spatial resolution are known. Other parameters such as the degree of cone beam distortion can also be helpful in this setting.

As noted above, an x-ray image can be transmitted from a local site into a remote server and the remote server can perform an automated analysis of the x-ray. Further, the remote server or a computer connected to the remote server can then generate a diagnostic report. Thus, in certain embodiments, a computer program (e.g., on the remote server or on a computer connected to the remote server) can generate charges for the diagnostic report. The remote server can then transmit the diagnostic report to a physician, typically the physician who ordered the test or who manages the patient. The diagnostic report can also be transmitted to third parties, e.g. health insurance companies. Such transmission of the diagnostic report can occur electronically (e.g. via e-mail), via mail, fax or other means of communication. All or some of the transmitted information (e.g., patient identifying information) can be encrypted to preserve confidentiality of medical records.

Thus, one exemplary system is described herein for analyzing bone morphology or structure in a subject system via a dental x-ray that includes at least a portion of the mandible and/or maxilla of a subject, followed by evaluation or the x-ray image. Dental x-rays are obtained in any conventional method. The x-ray produces an image that can be interpreted (for example, employing a selected algorithm and/or computer program) by an associated system controller to provide a bone mineral density or bone structure evaluation for display.

In a further aspect of the present invention, the monitoring system can comprise two or more components, in which a first component comprises an x-ray image and calibration phantom that are used to extract and detect bone-related data on the subject, and a second component that receives the data from the first component, conducts data processing on the data and then displays the processed data. Microprocessor functions can be found in one or both components. The second component of the monitoring system can assume many forms 3.0.0.0 Correction Factors Although the presence of calibration phantoms greatly aids in increasing the accuracy of data obtained from dental x-rays, the present inventors also recognize that, in certain instances, there may be a need to apply one or more correction factors to further enhance accuracy of the data obtained from any given x-ray image. Such correction factors will take into account one or more of a wide variety of influences (e.g.,. soft tissue thickness, region from which the data is extracted and the like) that can alter apparent density or structure information on the x-ray image.

3.1.0.0. Anatomical Landmarks

In one embodiment, identification of anatomic landmarks of the structure to be analyzed or identification of anatomical landmarks adjacent to the structure to be analyzed with subsequent positioning and computer analysis of the x-ray image relative to these anatomic landmarks or with subsequent positioning and computer analysis of anatomical region of interest (ROI) relative to these anatomic landmarks. The present invention includes also positioning dental x-ray detectors and analyzing the resulting images using landmarks based on either 1) textural information, 2.) structural information, 3.) density information (e.g. density), or 4) 2 or 3 dimensional contour information 5) a combinations thereof of the tissue or structure to be measured and of tissues or structures adjacent to the measurement site. The invention also includes methods and devices that are not necessarily based solely on anatomical landmarks, but in some applications can be combined with anatomical landmark embodiments. Preferably, many of the embodiments described herein are designed for automated use with a minimum of operator intervene and preferably remote or computer control of such devices.

The anatomical landmark that is selected is part of an anatomical region. An anatomical region refers to a site on bone, tooth or other definable biomass that can be identified by an anatomical feature(s) or location. An anatomical region can include the biomass underlying the surface. Usually, such a region will be definable according to standard medical reference methodology, such as that found in Williams et al., Gray's Anatomy, 1980. The anatomical region can be selected from the group consisting of an edge of the mandible, an edge of the maxilla, an edge of a tooth, valleys or grooves in any of these structures or combinations thereof. The dental x-ray image can be readily taken so as to include the anatomical site. Other anatomical regions include but are not limited to the hip, the spine, the forearm, the foot, and the knee.

For example, the region of interest is placed between the dental apices and the inferior mandibular cortex. The apices can be found automatically in the following way: for each row of pixels, the gray value profile is examined. While a profile that intersects bone and dental roots in an alternating fashion has several distinct peaks and valleys, a profile that only covers trabecular bone shows irregular changes in the gray values (FIG. 6). The dental apices are located in the transitional region between these two patterns.

The measurement techniques to assess trabecular bone structure are preferably designed to work without user intervention. In order to fully automate the process of analyzing dental x-rays, it is necessary to develop a technique to locate the regions of interest (ROIs) that are used for the calculation of the structural parameters of the trabecular bone. If the profile for a particular row of pixels contains distinct peaks, their number, width and height can be determined. Next, the rows below these lines can be evaluated until the peaks have disappeared. This line determines the boundary, 5 mm below which the ROI can be placed in the center between the longitudinal axes of the roots, which can also be determined from the row profiles (FIG. 6). At a pixel size of 0.042 mm×0.042 mm, which corresponds to a resolution of 600 dpi, the ROI has a size of 5.4 mm×5.4 mm (128×128 pixels). For other scanning resolutions, the pixel resolution of the ROI can be adjusted accordingly.

In the case of an edentulous patient, bone mineral density can be measured in all ROIs that are located on a line that is, for example, 8 mm inferior and parallel to the alveolar ridge. The ROIs can be moved from left to right on a pixel-by-pixel basis. Eventually, the ROI with the lowest BMD can be chosen for further evaluation of the structural bone parameters. This helps to avoid inclusion of regions on the x-ray where bone mineral density may be overestimated due to projection of the curved parts of the mandible near the canine teeth. Alternatively, the ROI with the median BMD can be used. Other statistical parameters can be employed for this purpose.

Thus, software or other computational unit can identify the selected anatomic landmark in an interrogated x-ray image and direct analysis of the image using various parameters and analytic functions. Further, such software or other computational analytical unit can be used to identify areas of particular density at a certain distance from the selected landmark. Similarly, manual or computer analysis can be used to identify areas of lowest, highest, median or average density (or structural characteristics) in relation to the selected landmark.

Further, the same landmark may be compared at different times (intra-landmark comparison) or one or more landmarks may be compared (inter-landmark comparison). For instance, an intra-landmark comparison can be used during a single interrogation protocol that entails multiple interrogations of the same region with reference to a particular anatomical landmark. Statistical analysis as described herein and known in the art can be performed.

3.1.1.0. Hough Transform

Additional, the Hough transform (See, e.g., Hough "Machine analysis of bubble chamber pictures" in International Conference on High Energy Accelerators and Instrumentation. 1959. CERN) can be used to detect geometric objects in binary images. As an entirely new approach to assessing bone structure, the invention includes the use of such methods to analyze direction and length of trabecular structures in bone x-ray images. For this purpose, the region of interest (ROI) can be blurred with a Gaussian filter. The pixel values of the filtered ROI can then be subtracted from those in the original ROI, and the value 128 can be added at each pixel location. This results in an image with a mean gray value of 128, which is also used as a threshold to yield a binary image in which the trabeculae are represented by the white pixels.

After a skeletonization step, a Hough transform with the line parameterization $\rho = x\cos\theta + y\sin\theta$ can be applied to the binary image in order to find straight line segments. Here $\rho$ is the perpendicular distance of the line from the origin and $\theta$ is the angle between the x-axis and the normal. Each point $(\hat{x}, \hat{y})$ in the original image is transformed into a sinusoidal curve $\rho = \hat{x}\cos\theta + \hat{y}\sin\theta$ in the $(\rho,\theta)$ plane of the transformed image (see FIG. 7)). Ideally, the curves from collinear points in the original image intersect in a single point in the transformed image. However, the $(\rho,\theta)$ plane can be divided into bins, where each bin counts the number of transformed curves that pass through it. This number corresponds to the number of collinear points on a line segment in the original image, and thus the length of this segment. Furthermore, the transformed image provides information on the predominant angles of the line segments in the original image (see FIG. 8).

The average length and the variance of the line segments, which are calculated for all bins with a count above a certain threshold, can be used as structural parameters for the shape of the bone trabeculae. Average length as well as the variability of the length to decrease in patients with osteoporosis. The threshold has the effect that only segments of a certain minimal length are included in the calculation. Choosing the threshold so that it provides the best discrimination between healthy and diseased individuals can be readily determined by one of skill in the art in view of the teachings herein.

The "center of mass" of the transformed image h, given as $$CM = \left(\sum_{(\rho,\theta)} (\rho, \theta)^T * H(\rho, \theta)\right) \bigg/ \sum_{(\rho,\theta)} H(\rho, \theta),$$

in which each bin is interpreted as an element with a mass equivalent to its count, is a way to measure the predominant angles of the trabecular segments. The angle at cm is measured with respect to the alveolar rim to obtain a standardized value. More importantly, the variance of the segment angles (again measured after thresholding the bin counts) provides information on the anisotropy of the trabecular structure. Histomorphological studies of osteoporotic vertebrae have shown that the variability of trabecular orientations decreases with the disease.

3.1.2.0. Analysis of Density and Size Distribution of Trabeculae

Morphological operations such as variations of dilation and erosion and combinations thereof can also be used to detect the size of structures in gray scale or binary images. For example, a skeleton operator can be used to extract and quantify trabeculae of different sizes and directions, which results in a measure of the size distribution of trabecular structures. This skeleton operator is based on the work described in Kumasaka et al. (1997) *Dentomaxllofac Rad* 26:161–168 and works as follows:

Let a two-dimensional structuring element e be a function over the window $-m \leq i,j \leq m(m>0)$ with $E(i,j) \in \{0,1\}$. The dilation operator sets a pixel value f(x,y) in a gray scale image f to the maximum of those values within the window of size m, for which e(i,j)=1:

$$[f \oplus E](x, y) = \max_{-m \leq i,j \leq m} \{f(x+i, y+j) \mid E(i, j) = 1\}$$

The erosion operator is defined accordingly, using the minimum instead of the maximum:

$$[f \otimes E](x, y) = \min_{-m \leq i,j \leq m} \{f(x+i, y+j) \mid E(i, j) = 1\}$$

'Opening' is the operation of maximum search after minimum search:

$$f_E = (f \otimes E) \oplus E$$

Accordingly, the 'closing' operation is defined as the minimum search after maximum search:

$$f^E = (f \oplus E) \otimes E$$

If a fixed structuring element $E_1$ is given as $E_1(i,j) = 1$ for $-1 \leq i,j \leq 1$, the skeleton operation is then defined as $$S_{Trabeculae}(f) = (f \otimes E_2) - [(f \otimes E_2)_{E_1}] \tag{1}$$

$E_2$ is another structuring element that is of circular shape and can be varied in size, and therefore renders the skeleton operator sensitive to the size of the structures in the image. The erosion of f with $E_2$ erases the structures that are smaller than $E_2$ and extracts those trabeculae that are at least equal in size. Those structures that are exactly equal in size is reduced to a width of one pixel. The opening step with $E_1$ causes all structures that are one pixel wide to disappear (second term in (1)). After subtraction of this term from the first one, only those trabecular structures that exactly match the size of $E_2$ remain. Finally, the image is thresholded with a level of 1. The effect of this operator is illustrated in FIG. 9.

FIG. 10 demonstrates the use of the skeleton operator with the same structural element diameters as in FIG. 9 on a gray scale region of interest from a dental x-ray containing trabecular bone. The number of bright pixels in the binary images resulting from each skeleton operation corresponds to the portion of trabeculae of the particular size in the original image. If the percentage of the bright pixels with respect to the total number of pixels in each skeletonized image is plotted against the diameter of $E_2$, the "center of mass" of the curve, i.e. the predominant structure size, can be used as an index to discriminate between osteoporotic and healthy bone.

Furthermore, the skeleton operator is preferably optimized and extended to detect structures that are oriented only in a specific direction. This can be achieved by adding erosion operations to the skeleton operator with structural elements in which, for example, only the diagonal pixels are set to 1.

This can be used to calculate an anisotropy index, similar to the one derived from the Hough transform. Both anisotropy indices are tested with respect to their potential to distinguish healthy from osteoporotic bone.

In a similar manner the sizes of the marrow spaces can be examined. The skeleton operator is then defined as $$S_{Marrow}(f) = (f \oplus E_2) - [(f \oplus E_2)^{E_1}]$$

3.1.3.0. Multidimensional Classification Schemes

In certain embodiments, it is preferred to use multiple indices to measure bone structure parameter. Thus, novel approaches that integrate one or more suitable indices can be employed The indices can be optimized and incorporated into a multi-dimensional classification scheme, for example using a nearest neighbor classification. Cover et al. (1967) *IEEE Trans Inform Theory* 13(1):21–7. (See, Example 3).

Table 1 provides examples of different analyses and anatomical/physiological correlates of the parameters that can be measured.

TABLE 1

| Analysis | Anatomical/Physiological Correlates |
|---|---|
| Hough transform | length and direction of trabeculae; anisotropy |
| Morphological operators | thickness and direction of trabeculae; anisotropy; thickness and length of marrow spaces |
| Mean pixel intensity | bone mineral density |
| Variance of pixel intensity | complexity of trabecular structure |
| Fourier spectral analysis | complexity of trabecular structure |
| Fractal dimension | complexity of trabecular structure |
| Morphological parameters | length, size of trabeculae; complexity of trabecular structure; length, size of marrow spaces; complexity of marrow space |

3.1.3.1 Mean pixel intensity

Mean pixel intensity is a general parameter for the bone mineral density. The degree to which x-rays passing through bone tissue are absorbed depends on the bone's mineral content. Bone with a higher mineral density absorbs a larger portion of x-rays, and therefore appears brighter on the x-ray image.

The mean pixel intensity $\overline{f(x,y)}$ in the ROI is calibrated against an aluminum calibration wedge that is included in the image. The log of the average pixel intensity for each thickness level of the calibration wedge is plotted against the thickness, which allows $\overline{f(x,y)}$ to be converted into a standardized aluminum thickness equivalent, which is used as the value for this parameter. The automatic recognition of the different thickness levels of the calibration wedge are made possible by different geometric patterns scribed into the wedge which are shown in the x-ray image and can be localized automatically.

3.1.3.2. Variance of pixel intensity

The variance of the pixel gray values in the roi, var f(x,y), describes the variability of the pixel intensities and can therefore be a measure of the degree of trabeculation. A loss of trabecular bone is predicted to be reflected by a decreased var f(x,y). Southard & Southard (1992) *Oral Surg Oral Med Oral Pathol* 74:111–117.

3.1.3.3. Fourier spectral analysis

The spatial frequency spectrum of a texture provides information about its coarseness. Fine textural structures and edges in an image correspond to high frequencies in the frequency domain, while coarse textures are represented by lower frequencies. Applied to x-ray images of trabecular bone, this means that a region with coarse or little trabeculation should exhibit a Fourier spectral energy concentration at low spatial frequencies, whereas a region of fine trabecular structure should show a spectral energy concentration at high frequencies.

Typically, the 2-dimensional Fourier coefficients for the selected ROI. These 2-dimensional coefficients are used to determine a 1-dimensional power spectrum F(u) by averaging all coefficients over circles with radii that correspond to the discrete spatial frequencies u. The mean transform coefficient absolute value $\overline{|F(u)|}$ and the mean spatial first moment $$M_1 = \frac{\sum_{u=2}^{N} |F(u)| \cdot u}{N-1}$$

of the absolute coefficients are determined after exclusion of the first ("DC") coefficient $M_1$ provides a measure for which frequencies contribute most to the energy of the spectrum, similar to the "center of mass" of a geometric object 3.1.3.4. Fractal dimension A different approach to analyze the texture in an image is by fractal analysis. Fractals are objects that exhibit certain statistical self-similar or self-affine properties, so that a portion of the object, scaled to its original size, has for example the same surface area (3-d) or the same perimeter (2-d) as the original object. In the context of fractal analysis, the gray values in a particular texture can be interpreted as an altitude, and the resulting 3-dimensional surface is analyzed (FIG. 11).

Fractal dimension (fd) is the rate at which the perimeter or surface area of an object increases as the measurement scale is reduced. Russ "The Image Processing Handbook," Third edition ed. 1999, Boca Raton: CRC press. It is a measure for the complexity of a boundary or surface and corresponds to the intuitive notion of an object's roughness. Without being bound by one theory, it is postulated that osteoporotic trabecular bone, in which trabeculae become thinner and lose their continuity, and therefore complexity is increased, should have a higher fractal dimension than healthy bone.

The results from the several ways in which FD can be measured are not comparable. Thus, various methods can be tested to determine which one (or combination) provides the best discrimination between normal and osteoporotic subjects.

The first method is applied in the frequency domain after calculation of the ROI's 2-D power spectrum using a fast Fourier transform (FFT). From the 2-D Fourier coefficients the 1-D power spectrum is produced as described above for the Fourier analysis. When this 1-D power spectrum is plotted as the logarithm of the power versus the logarithm of the frequency, it must have a negative slope of magnitude b with 1<b<3 according to fractal theory. The FD value is then calculated as $FD_1=3.5-b/2$.

Another approach, the Minkowski method, measures the difference (summed over the ROI) between an upper and lower envelope fitted to the surface as a function of the size of the neighborhood used. Peleg et al. (1984) *Anal Mach Intell* 6(4):518–523. If $\delta$ ($\delta=1,2,3,\ldots$) is the distance between the envelopes and the surface, then the upper envelope $u_\delta$ and the lower envelope $1_\delta$ are given by $$u_0(i, j) = l_0(i, j) = f(i, j)$$

$$u_{\delta+1}(i, j) = \max\left\{u_\delta(i, j) + 1, \max_{\|(m,n)-(i,j)\|\leq 1} \{u_\delta(m, n)\}\right\}$$

$$l_{\delta+1}(i, j) = \min\left\{l_\delta(i, j) - 1, \min_{\|(m,n)-(i,j)\|\leq 1} \{l_\delta(m, n)\}\right\}$$

where f(i,j) is the gray value of pixel (i,j) in the ROI. The log of the area $A(\delta)$, plotted against $\log(\delta)$, yields a line with a negative slope of magnitude b'. The fractal dimension is then given by $FD_2=2-b'$. The area is calculated as $$A(\delta) = \frac{v_\delta - v_{\delta-1}}{2}$$

with $$v_\delta = \sum_{(i,j) \in ROI} (u_\delta(i,j) - l_\delta(i,j)).$$

3.1.3.5. Morphological Parameters

While the previous features and parameters provide rather general information on trabecular bone structure, the following examples describe more detailed aspects.

The gray scale region of interest is first binarized. As described in White et al. (1999) *Oral Surg Oral Med Oral Patholo Oral Radiol Endod* 88:628–635, this can be achieved in the following way: The ROI is blurred by means of a Gaussian filter. The blurred ROI is then subtracted from the original ROI, and the value 128 is added at each pixel location. This results in an image with a mean gray value of 128, which is also used as a threshold, resulting in an image, in which trabeculae are white and marrow space is black.

From this binary image, the total number of white pixels represents the trabecular area, which is calculated as a percentage of the total ROI area. The number of pixels on the outer trabecular border measures the peripheral length of the trabeculae. The same parameters can be measured for the marrow space by counting the black pixels.

After skeletonization of the binary image, the total length of the trabeculae is determined by the total number white pixels. Furthermore, the counts of the terminal points and of the branch points are expressed as a proportion of trabecular length. An estimate of the average length of the trabeculae is calculated as the ratio of total trabecular length and the sum of terminal points and branch points.

3.2.0.0. Soft Tissue

Variations in soft tissue thickness can be significant in analyzing and evaluating bone density and bone structure in x-rays. Accordingly, the invention also includes methods and devices for correcting for soft tissue in assessment of bone structure or dense tissue, particularly for diagnosing and/or predicting osteoporosis or other bone conditions.

In certain embodiments, the x-ray image is a dental x-ray image and such correction methods involve (a) interrogating at least a portion of a subject's mandible and/or maxilla with an x-ray detector, (b) producing an x-ray image of the interrogated mandible and/or maxilla; (c) obtaining data from the x-ray image regarding bone density or bone structure; (d) interrogating the surrounding soft tissue to determine soft tissue thickness; and (e) correcting the data obtained from the x-ray image by correcting for soft tissue thickness. Such study groups include: non-osteoporotic premenopausal, non-osteoporotic postmenopausal, osteoporotic postmenopausal patients. It will be apparent, although exemplified with respect to dental x-rays, that many of the methods described herein can be applied to other x-ray images.

Soft tissue thickness measured in a subject can also be compared to reference soft tissue thickness obtained from a control population (e.g age-, sex-, race-, or weight-matched normal subjects). Reference soft tissue thickness can be generated by measuring soft tissue thickness in healthy subjects with normal vascular, cardiac, hepatic, or renal function and no other underlying medical condition. Reference soft tissue thickness can be expressed as but are not limited to, mean and standard deviation or standard error. Reference soft tissue thickness can be obtained independently for patients 15–20, 20–30, 30–40, 40–50, 50–60, 60–70, 70–80, and 80 and more years of age and are preferably obtained separately for men and women and for race (e.g. Asian, African, Caucasian, and Hispanic subjects). Additionally, reference soft tissue thickness can be obtained for different subject weights within each age, sex, and racial subgroup.

Individual patients can be compared to reference soft tissue thickness. If patient's soft tissue thickness is elevated, a correction factor can be applied. The amount/magnitude of correction factor is influenced by the magnitude of increase in soft tissue thickness that can be influenced by the magnitude of fat, fibrous, and muscle tissue contribution. Clinical study groups can be evaluated to generate databases for further study or to generate more refined correction factors. Such study groups include: non-edematous non-osteoporotic premenopausal non-edematous non-osteoporotic postmenopausal, non-edematous osteoporotic postmenopausal; edematous non-osteoporotic premenopausal, edematous non-osteoporotic postmenopausal, and edematous osteoporotic postmenopausal patients. In each study group the following procedures can be performed for comparison: dual x-ray absorptiometry ("DXA") of the spine, hip, or calcaneus, along with SOS and BUA measurements or quantitative computed tomography ("QCT"). Thus, correction for soft tissue thickness can also improve the accuracy and discriminatory power in the analysis of x-rays and other x-rays. Such methods can also be used to identify population with an increased or decreased risk of bone conditions such as osteoporosis.

3.2.1.0. Soft Tissue Correction Devices

Current dental x-ray films and detectors are hand positioned relative to the teeth to be imaged. Accordingly, the resulting image may or may not include anatomical landmarks of the mandible or maxilla and, additionally, the image does not necessarily account for variation in soft tissue thickness.

Figure 12:
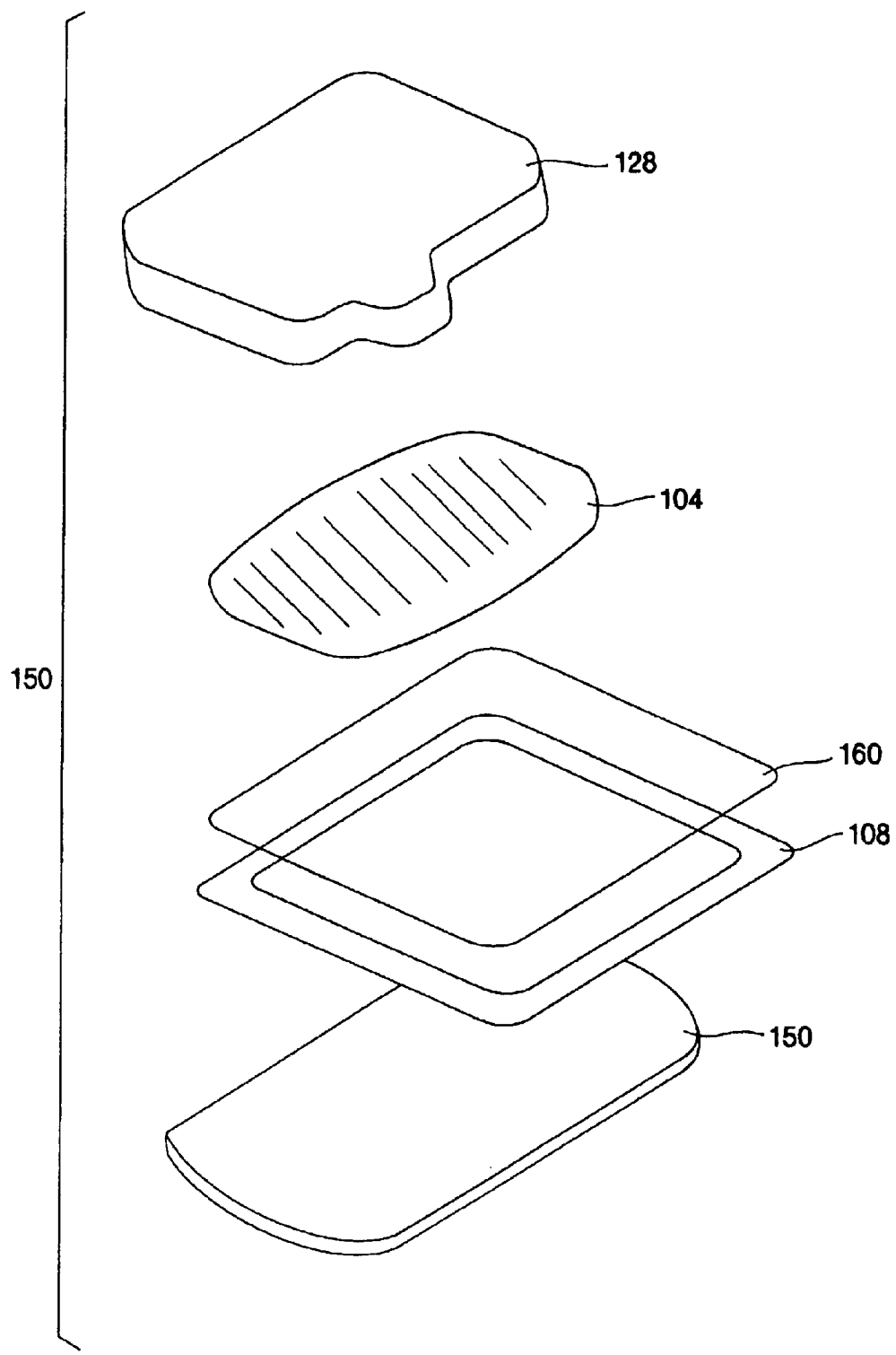
FIG. 12 shows an example of a hygienic cover holder that includes compartments for a calibration phantom and a fluid-filled bolus back.
Figure 13:
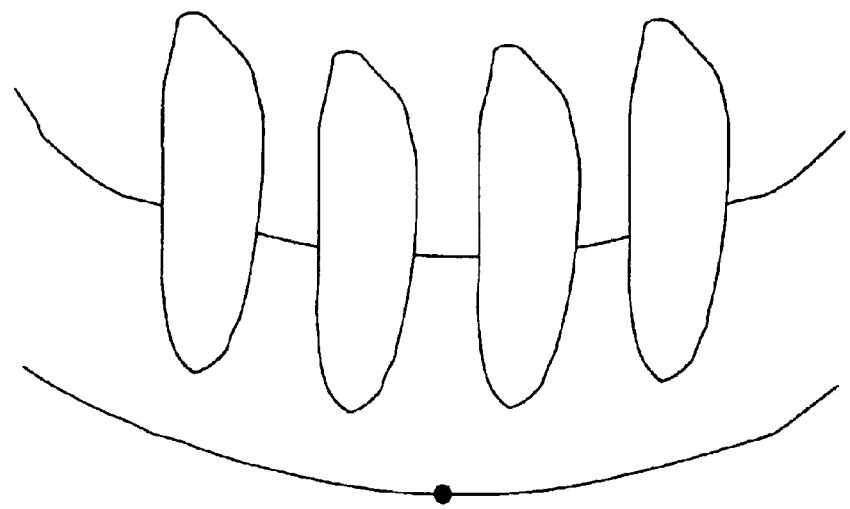
FIG. 13 shows an example of an anatomical region of interest (black dot), determined relative to the teeth or to the convexity/concavity of the mandible.
Figure 14:
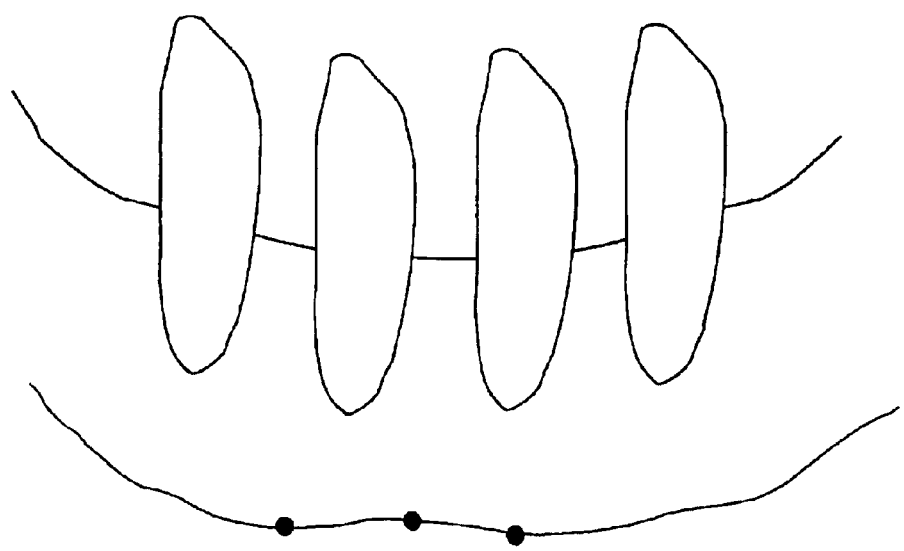
FIG. 14 shows an example of three anatomical region of interests (black dots), determined relative to the teeth or to the convexity/concavity of the mandible.

Referring to FIG. 12, showing an exploded view of exemplary components comprising one embodiment of a holder assembly for a calibration phantom for use in a dental x-ray imaging system is presented. The calibration phantom 104 includes reference materials in the any of the shapes described above, each of which has a known density and/or spacing. The calibration phantoms can be integrated into the holder or placed in a compartment within the holder (or hygienic cover). Thus, the hygienic cover 150 is preferably arranged over the calibration phantom. Additionally, the hygienic cover be adapted to receive dental x-ray film 108, for example within a pocket or compartment of the cover. Further liners and/or compartments may be included in the assembly, for example, a liner 160 between the calibration phantom reference wedges, the hygienic cover and/or the bolus.

A bolus back 128 may be included in the calibration phantom assembly, for instance to help with soft-tissue correction. Preferably, the bolus back is filled with fluid or gel. Non-toxic fluids such as water or saline are preferred. The bolus back is positioned such that the beam of the x-ray projects through it and, accordingly, onto the resulting image. Because the bolus back is of known thickness and composition and has an x-ray density similar to soft-tissue and its effect on the x-ray image is known, it is able to correct for variability caused by soft tissue.

The hygienic cover, liners and/or bolus are preferably composed of (or covered by) materials that are substantially impermeable saliva and other bodily fluids and/or substances. By "substantially impermeable" is meant that the material reduces or eliminates transport (e.g., by diffusion). The material can allow for a low level of transport with the proviso that the material that passes through the material does not cause significant effects on the x-ray image or on the calibration phantom reference wedges. Examples of materials that can be used to form the layers include, but are not limited to, polyester, polyester derivatives, other polyester-like materials, polyurethane, polyurethane derivatives and other polyurethane-like materials or polyethylenes.

Soft tissue correction devices can also include one or more means of compressing the soft tissue to a particular thickness. The compressive element can be virtually any shape and can be manually or automatically placed in contact with and pressed again the soft tissue to be compressed.

4.0. Applications

The measurements of bone mineral density or trabecular architecture in the mandible or said maxilla can be used to derive an assessment of bone health in any subject. Additionally, the analysis and manipulation of data from x-rays allows for the assessment of bone health that in turn can be used to prescribe a suitable treatment regime. Efficacy of a treatment regime can also be assessed using the methods and devices described herein (for example, using measurements of bone mineral density or trabecular architecture in the mandible or the maxilla taken at two separate time points T1 and T2 to detect any difference in bone mineral density or trabecular architecture).

4.1. Kits

The invention also provides kits for obtaining information from x-ray images, for example for obtaining information regarding bone structure from an x-ray such as a dental x-ray. In certain embodiments, the kit comprises one or more computer (e.g., software) programs, for example for receiving, analyzing and generating reports based on x-ray images. In further embodiments, the kits can include calibration phantoms, for example calibration phantoms integrated or attachable-to a holder, hygienic cover, x-ray film and/or x-ray film holders.

The invention also provides for therapeutic kits, for example for treating osteoporosis or dental disease. In certain embodiments, the kits comprises an x-ray image, a calibration phantom, a computer software product, a database and a therapeutic drug. The therapeutic drug can be anti-resorptive or anabolic.

4.2. Diagnosis and Prediction

In yet another aspect, methods of diagnosing or predicting bone-related disorders (e.g., osteoporosis, Paget's Disease, osteogenesis imperfecta, bone cancers), periodontal disease or oral implant failure in a subject are provided, for example using any of the kits, methods and/or devices described herein. It will be apparent that these methods are applicable to any bone-related disorder including, for example, osteoporosis, bone cancer, and the like, as well as to periodontal disease and implant failure.

Osteoporosis alone is a major public health threat for 25 million postmenopausal women and 7 million men. In 1995, national direct expenditures for osteoporosis and related fractures were $13 billion. Changing demographics, with the growth of the elderly population, steadily contribute to increasing numbers of osteoporotic fractures and an incipient and potentially economically unmanageable epidemic of osteoporosis. Projections put the total cost of osteoporosis in the United States alone at more than 240 billion dollars per year in 40 years.

Less than 20% of the patients know they have the disease and many fewer receive physician directed specific therapy. A major impediment in successfully dealing with the impending osteoporosis epidemic is not a lack of treatment modalities but the inability to identify persons at risk and who require treatment. The limited access to osteoporosis testing is largely the result of the high cost of the currently available systems resulting in a small installed base limited to hospitals and specialty clinics.

The devices and methods described herein address these and other issues by providing inexpensive and reliable bone structural analysis screens and resulting diagnosis of bone condition and/or presence of disease. Indeed, while measurements of bone mineral density (BMD) are technically relatively easy to perform, low BMD accounts for considerably less than 100% of fracture risk although it is well established that progressive disruption of trabecular structure and architecture contribute in a major way to fracture risk in older individuals.

Thus, in certain embodiments, the methods comprise using a computer program to analyze bone mineral density or bone structure of a x-ray image (e.g., dental x-ray image) and comparing the value or measurement obtained from the image with a reference standard or curve, thereby determining if the subject has a bone-related condition such as osteoporosis. The x-ray image can also include a calibration phantom, for example a calibration phantom as described herein.

4.3. Treatment

The methods and devices described herein can also be used to develop an appropriate treatment regime for a subject in need thereof. Additionally, the invention allows for the ongoing analysis of the efficacy of a subject's treatment regime.

Although estrogen deficiency after menopause is one of the most well documented causes of osteoporosis that can be prevented by hormone replacement therapy (HRT), HRT may also cause an increase (approximately 35%) in the risk of breast cancer in long-term users. *Lancet* (1997) 350:1047–1059. Consequently, much effort has been devoted to developing alternative treatments for osteoporosis. Among those treatments, bisphosphonates are becoming increasingly recognized as the treatment of choice. Lin (1996) *Bone* 18:75–85; Liberman et al. (1995) *N Engl J Med* 333:1437–1443; Mortensen et al. (1998) *J Clin Endocrinol Metab* 83:396–402. Another new class of therapeutic agents recently introduced is the selective estrogen receptor modulators (SERMs). Delmas et al. (1997) *N Engl J Med* 337:1641–1647; Lufkin et al. (1998) *J Bone Min Res* 13:1747–1754. Anabolic therapies such as parathyroid hormone have also been suggested for treatment of osteoporosis. Roe et al. (1999) *J Bone Miner Res* 14(supp11):S137, Abst#1019; Lane et al. (1998) *J Clin Invest* 102:1627–33.

The combined results of these and other studies suggest that effective treatments for osteoporosis can be developed once the condition is diagnosed. For instance, using any of the methods, kits, and/or devices described herein, the presence of osteoporosis in a subject can be diagnosed and that subject provided with appropriate therapy (e.g., one or more anti-resorptive agents and/or one or more anabolic agents). Periodontal disease can be similarly diagnosed and treatments ranging from oral hygiene practices to surgery can be recommended. Over time, the methods described herein can be used to assess the efficacy of the selected treatment and the treatment regime altered as necessary. Thus, in certain embodiments, treatment of bone related disorders are provided.

4.4. Decision Trees

Thus, diagnosing, predicting, developing treatment regimes, assessing treatment efficacy and the like can be readily accomplished using the methods described herein. In certain aspects, these applications will be accomplished using algorithms or decision trees (also known as logic trees or flow charts). One exemplary decision tree is providing in regard to predicting bone problems. It will be readily apparent that such decision trees are equally applicable to other applications (e.g., designing treatment regimes, assessing treatment efficacy, etc.).

One exemplary method for predicting bone problems (e.g., osteoporoses, etc.), periodontal disease or oral implant failure employs a decision tree (also called classification tree) which utilizes a hierarchical evaluation of thresholds (see, for example, J. J. Oliver, et. al, in Proceedings of the 5th Australian Joint Conference on Artificial Intelligence, pages 361–367, A. Adams and L. Sterling, editors, World Scientific, Singapore, 1992; D. J. Hand, et al., Pattern Recognition, 31(5):641–650, 1998; J. J. Oliver and D. J. Hand, Journal of Classification, 13:281–297, 1996; W. Buntine, Statistics and Computing, 2:63–73, 1992; L. Breiman, et al., "Classification and Regression Trees" Wadsworth, Belmont, Calif., 1984; C4.5: Programs for Machine Learning, J. Ross Quinlan, The Morgan Kaufmann Series in Machine Learning, Pat Langley, Series Editor, October 1992, ISBN 1-55860-238-0). Commercial software for structuring and execution of decision trees is available (e.g., CART (5), Salford Systems, San Diego, Calif.; C4.5 (6), RuleQuest Research Pty Ltd., St Ives NSW Australia) and may be used in the methods of the present invention in view of the teachings of the present specification. A simple version of such a decision tree is to choose a threshold bone structure or bone mineral density reading at a particular anatomical landmark (e.g., edge of mandible or maxilla, the end of a tooth root, etc.). If a value is equal to or below the threshold bone data value, then more of the image is evaluated. If more of the image is below the threshold value, then a bone problem, periodontal disease or implant failure is predicted.

For example, a first level decision is made by the algorithm based on the most recent x-ray images obtained and analyzed as described herein is compared to initial thresholds that may indicate an impending or current bone- or periodontal-related event. For example, the algorithm may compare the current bone structure measurements (time=n) or a predicted bone structure measurement (time=n+1) to a threshold value. If the bone structure measurement is greater than the threshold value then a decision is made by the algorithm to suggest further future x-rays. If the bone structure measurement is less than or equal to the threshold level(s) then the algorithm continues with the next level of the decision tree.

The next level of the decision tree may be an evaluation of the subject's age and/or gender at time (n) that x-ray is taken, which is compared to a threshold bone measurement for "normal" subjects of that age and/or gender. For example, if the subject's bone measurement is greater than the threshold bone structure level for that particular age and/or gender, then a decision is made by the algorithm to prompt further monitoring in the future. If the information on bone structure is less than or equal to the threshold, then the algorithm continues with the next level of the decision tree.

The next level of the decision tree may be, for example, an evaluation of the subject's soft tissue (e.g., gum) thickness (n), which is compared to a threshold measurement. For example, if the soft tissue is significantly below or above the normal range of thickness, then a decision is made by the algorithm to examine more of the x-ray image or to predict a bone-related problem.

The decision tree could be further elaborated by adding further levels. For example, after a determination that a bone and/or periodontal events are possible, the subject can be x-rayed again to see if values have changed. Again, age, gender, weight, soft tissue thickness and the like can also be tested and considered to confirm the prediction.

In such decision trees, the most important attribute is typically placed at the root of the decision tree. In one embodiment of the present invention the root attribute is the current bone structure measurement(s). In another embodiment, a predicted bone structure measurement at a future time point may be the root attribute. Alternatively, bone mineral density and/or implant structure could be used as the root attribute.

Further, thresholds need not (but can) be established a priori. The algorithm can learn from a database record of an individual subject's readings and measurements. The algorithm can train itself to establish threshold values based on the data in the database record using, for example, a decision tree algorithm.

Further, a decision tree may be more complicated than the simple scenario described above. For example, if soft tissue of a particular subject is very thick, the algorithm may set a threshold for the bone measurements that is higher or lower than normal.

By selecting parameters (e.g., current or future bone information, etc.) and allowing the algorithm to train itself based on a database record of these parameters for an individual subject, the algorithm can evaluate each parameter as independent or combined predictors of disease and/or implant failure. Thus, the prediction model is being trained and the algorithm determines what parameters are the most important indicators. A decision tree may be learnt in an automated way from data using an algorithm such as a recursive partitioning algorithm. The recursive partitioning algorithm grows a tree by starting with all the training examples in the root node. The root node may be "split," for example, using a three-step process as follows. (1) The root node may be split on all the attributes available, at all the thresholds available (e.g., in a training database). To each considered split a criteria is applied (such as, GINI index, entropy of the data, or message length of the data). (2) An attribute (A) and a threshold (T) are selected which optimize the criteria. This results in a decision tree with one split node and two leaves. (3) Each example in the training database is associated with one of these two leaves (based on the measurements of the training example). Each leaf node is then recursively split using the three-step process. Splitting is continued until a stopping criteria is applied. An example of a stopping criteria is if a node has less than 50 examples from the training database that are associated with it.

In a further embodiment, at each level of the decision in the decision tree, the algorithm software can associate a probability with the decision. The probabilities at each level of decision can be evaluated (e.g., summed) and the cumulative probability can be used to determine whether disease and/or implant failure is predicted. Receiver Operating Characteristic (ROC) curve analysis can be applied to decision tree analysis described above. ROC analysis is another threshold optimization means. It provides a way to determine the optimal true positive fraction, while minimizing the false positive fraction. A ROC analysis can be used to compare two classification schemes, and determine which scheme is a better overall predictor of the selected event (e.g., evidence of osteoporosis); for example, a ROC analysis can be used to compare a simple threshold classifier with a decision tree. ROC software packages typically include procedures for the following: correlated, continuously distributed as well as inherently categorical rating scale data; statistical comparison between two binormal ROC curves; maximum likelihood estimation of binormal ROC curves from set of continuous as well as categorical data; and analysis of statistical power for comparison of ROC curves. Commercial software for structuring and execution of ROC is available (e.g., Analyse-It for Microsoft Excel, Analyse-It Software, Ltd., Leeds LS12 5XA, England, UK; MedCalc®, MedCalc Software, Mariakerke, Belgium; AccuROC, Accumetric Corporation, Montreal, Quebec, Calif.).

Related techniques that can be applied to the above analyses include, but are not limited to, Decision Graphs, Decision Rules (also called Rules Induction), Discriminant Analysis (including Stepwise Discriminant Analysis), Logistic Regression, Nearest Neighbor Classification, Neural Networks, and Naive Bayes Classifier.

All of these aspects of the invention can be practiced separately or in combination. Typically, the use of combinations of the embodiments listed above is more advantageous. Further, although preferred embodiments of the subject invention have been described in some detail it is understood that obvious variations can be made without departing from the spirit and the scope of the invention.

EXPERIMENTAL

Below are examples of specific embodiments for carrying out the present invention. The examples are offered for illustrative purposes only, and are not intended to limit the scope of the present invention in any way.

EXAMPLE 1

Calibration Phantom Inserted Into Hygienic Cover

The workflow presented herein constitutes one example for the use of a calibration phantom with the image acquisition. One skilled in the art will readily recognize other ways to include a calibration phantom in the acquisition process in order to normalize or standardize any form of measurement made from the x-ray image.

In this example, the calibration phantom is inserted into the compartment of a hygienic cover adapted to receive it. The hygienic cover is disposable. The calibration phantom includes geometrical patterns that provide a reference for bone structural characteristics. Dental x-ray film is also placed in a light-proof compartment in the hygienic cover. The assembly with the film and calibration phantom is positioned inside the patient's mouth in such a way that the calibration phantom is not obstructed from the x-ray beam by any structures such as teeth or the lips etc.

After acquisition of the image, the film is taken to the darkroom and the cover with the calibration phantom is removed. The film is then processed in the same way as a conventional dental x-ray film. The image is digitized and analyzed by one or more indices.

EXAMPLE 2

In vivo Reproducibility

In order to test in vivo reproducibility of data obtained from dental x-rays, the following experiment was performed. Subjects were asked to sit down in a dental chair and have an x-ray taken of the area of the incisor teeth and of the molar teeth of the mandible. A calibration phantom step wedge was attached to the dental x-ray film. The dental x-ray film was exposed using standard x-ray imaging techniques for x-rays of the incisor area. The subjects were asked to get up from the dental chair and walk around. The test was repeated 15 min later using the same procedure.

X-ray films were digitized on a commercial flat-bed scanner with transparency option (Acer ScanPremio ST). The regions of interest (ROIs) were placed manually at the same position with respect to the dental roots in all digitized x-rays of the same subject using the NIH Image software program (http://rsb.info.nih.gov/nih-image/Default.html). The reproducibility of the measurement of the average gray values inside the ROIs was determined as the coefficient of variation (COV=standard deviation of measurements/mean of measurements). Overall results are given as root mean square (RMS=$\sqrt{\Sigma_1^n x_i^2/n}$) over both subjects. The data are summarized in Table 2.

TABLE 2

| Reproducibility of measurements of average gray values in digitized dental x-rays | | | |
|---|---|---|---|
| Region | COV Subject A | COV Subject B | RMS |
| Incisor | 2.9% (n = 3) | 5.9% (n = 3) | 4.6% |
| Molar | 3.0% (n = 3) | 4.1% (n = 4) | 3.6% |
|  |  | All regions: | 4.2% |

The data show that reproducibility is achieved that is already comparable with that of many ultrasound systems to diagnose osteoporosis.

EXAMPLE 3

Multidimensional Classification

For each parameter a single scalar index value is calculated. All index values are combined into one n-dimensional feature vector. In a first step, the system will be trained with the data from our clinical validation study with 50 premenopausal 50 postmenopausal healthy and 50 postmenopausal osteoporotic subjects. These three subject groups will be divided into a "fracture" and a "no fracture" category. The feature vectors calculated from the dental x-ray images of these subjects is used as prototype patterns.

For each new patient, a feature vector is calculated from the x-ray in exactly the same way as the prototype patterns. This patient can now be classified as category C, if the majority of the k closest prototype patterns belongs to category C. The distance d between the patient's feature vector $f=(f_1, f_2, \ldots, f_n)^T$ and a prototype pattern $p=(p_1, p_2, \ldots, p_n)^T$ is defined by the Euclidean norm $L_2$:

$$d(f, p) = L_2(f, p) = \sqrt{\sum_{i=1}^{n} (f_i - p_i)^2}$$

The optimum scale for the different parameters is determined. However, for some parameters differences in the index values between the categories is smaller than for others. Also, the optimum k will be determined. Increasing k is expected to improve the accuracy of the classification, but it has to be smaller than the number of prototypes in each category. The exact percentage value of the majority of the k closest prototype patterns that determines the classification provides a measure for the reliability of the classification. The higher the percentage of prototype patterns from a particular category C is, the more significant is the information provided by the classification.

This classification approach is validated with a series of leave-one-out experiments. For these experiments, each subject is used as a test case exactly once. In each case, the training set for the system consists of the patterns calculated for all remaining subjects, and it is checked if the test case can be correctly classified using this training set.

In addition to the measurements described above (which provide index values for the parameters "length of trabeculae", "direction of trabeculae and anisotropy", and "trabecular thickness"), additional measurements for other parameters in the classification system that have been explored in the past to study bone density and structure from x-ray, CT, and MR images such as: (1) mean pixel intensity, (2) variance of pixel intensity; (3) Fourier spectral analysis; (4) fractal dimension; (5) morphological parameters such as the trabecular area, trabecular periphery, total trabecular length, number of terminal and branch points, as well as similar parameters for the bone marrow can be used.

EXAMPLE 4

Data Analysis

Patients are selected into one of three groups: healthy premenopausal (PRE); healthy postmenopausal (POST), and osteoporotic postmenopausal (OSTEO) women. All groups are studied by: (1) dental x-ray images of the periapical and canine region; (2) quantitative computed tomography of the spine and (3) hip; (4) dual x-ray absorptiometry of the spine and (5) hip; (6) single x-ray absorptiometry of the calcaneus, and (7) ultrasound of the calcaneus using standard techniques. The diagnosis of osteoporosis is defined as the presence of at least one atraumatic vertebral fracture as determined by a semi-quantitative assessment of morphologic changes of the thoracic and lumbar spine on lateral conventional x-rays.

The means and standard deviations of the different bone structure measurements (see above) and bone mineral density measurements (mandibular BMD, QCT spine, QCT hip, DXA spine, DXA hip, SXA calcaneus, ultrasound calcaneus) are calculated for each patient group. The Student's t-test (t-values and p-values) and percent decrement are used for comparing the different measurements for reflecting intergroup differences. Annual, age-related changes are expressed as percent changes relative to the predicted values at age 30 and as fractional standard deviation (SD) of PRE. Correlations with age along with p-values are also be reported. Odds ratios (for 1SD change in the measured parameter) and 95% confidence limits based on the age-adjusted logistic regression are calculated to measure the discriminative ability (for discriminating between the postmenopausal osteoporotic and the normal postmenopausal group) and the risk of osteoporotic fracture associated with the measured parameter. The pairwise comparisons of the discriminative abilities are tested using age-adjusted receiver operating characteristic (ROC) curve analysis.

Pairwise comparisons of all techniques are obtained by pooling all subjects (PRE, POST, OSTEO) and using Pearson's correlation coefficients (r), percent standard errors of the estimate (CV), and p-values for testing significance of correlations.

To compare measurements for their diagnostic ability, a kappa score analysis is performed on the normal postmenopausal women (POST) and the osteoporotic postmenopausal women (OSTEO). This is done by classifying every woman from the postmenopausal groups as osteopenic if her T-score with respect to the reference group (PRE) is less (or in case of structural parameters also greater) than 2.5. The T-score for an individual woman and a particular measurement is defined as the measurement minus the mean measurement of young normals (PRE) divided by the SD of the measurement in the PRE group. Note that the T-score is measuring the position of an individual woman with respect to the PRE group and is different from the Student's t-value.

EXAMPLE 5

Longitudinal Monitoring of Bone Structure

Algorithms and software to match follow-up dental x-rays obtained at a time point $T_2$ relative to baseline x-rays of the mandible obtained at an earlier time point $T_1$ are developed. For purposes of monitoring of therapeutic response, bone structure parameters have to be measured at the same location of the mandible at different points in time. Thus, in order to compensate for differences in patient positioning and in order to find corresponding regions of interest (ROI's) for comparison of the results between baseline and follow-up examinations, it is desirable register two dental x-ray images.

Due to possible slight differences in the projection angle of the x-ray beam on the film in the two images to be registered, an elastic matching step is included. The first step, however, is a global affine transformation, for which the mutual information is used as a cost function. Wells et al. (1996) *Medical Image* Analysis 1:35–51. The mutual information $I_{M,N}$ of two images M and N is defined as $$I_{M,N} = \sum_{(m,n)} p_{MN}(m,n) \log\left(\frac{p_{MN}(m,n)}{p_M(m)p_N(n)}\right).$$

Here, the gray values occurring in the two images are regarded as random variables, and the mutual information provides a measure of the strength of the dependence between these variables. $p_M$ and $p_N$ are the distributions of M and N respectively, and $p_{MN}$ is the joint distribution of M and N. Maintz et al. (1998) SPIE Medical Imaging-Image Processing. These distributions can be approximated from the marginal and joint gray value histograms, more accurately with the use of a Parzen window function. Powell's method can be used as an optimization scheme to find the best affine transformation for N to match it with M. Press et al. ("Numerical Recipes in C." 2nd edition, 1992, Cambridge University Press.

This global transformation is followed by local elastic adjustments to improve the match. To achieve this, the conditional probability densities p(n|m) are estimated from the joint histogram of the globally registered images. The transformation vector field t(x) is then determined such that N(x−t(x)) is as similar to M(x) as possible by maximizing the local gray value correspondence, which for a fixed value of x is defined as $$c_x(t) = \int w(x'-x) p(N(x'-t)|M(x')) dx'.$$

Here, w is a window function whose width determines the size of the region that is used to compute t(x). To determine the window function, an approach similar to the one described in Warfield et al. "Brain Warping" 1999, Academic Press, p:67–84 is used. A number of successively wider window functions $w_i$ are combined into a single window $$w = \sum_i W_i w_i,$$

where the weights $W_t$ are given as $$W_i = \frac{1}{\sum_i \det(Q_i)} \det(Q_i) \text{ with } Q_i = \int w_i(x' - x) \nabla N(x') \nabla N^T(x') dx'.$$

The exact location of the ROI after automatic placement in the baseline image for a particular patient is kept in a database. When the patient returns for a follow-up exam, the new image is registered with the baseline image, and thus transformed into the coordinate system of the baseline image. The bone structure in the registered follow-up x-ray can then be measured at exactly the same position as in the baseline image.

EXAMPLE 6

Edentulous Patients

Because it is difficult to match position in edentulous patients, a different approach is used with these patients to compare measurements from x-rays taken at different times.

The alveolar rim of the mandible is located using a Sobel edge detector followed by a thresholding step. On a line 10 mm below and parallel to the alveolar rim, a sliding ROI is moved in increments of one pixel, and the bone structure parameters are calculated for each position of the ROI. For each parameter, the software chooses the lowest or highest value, depending on which is the strongest indicator for the presence of osteoporosis. For the mean pixel intensity, for example, this would be the lowest value. The procedure is repeated on follow-up examinations. In this fashion, the software automatically detects the regions of maximum or minimum value 10 mm below and parallel to the alveolar rim. These maximum or minimum values can then be compared longitudinally over time.

What is claimed is:

1. A method to derive quantitative information on bone structure from a dental x-ray image comprising:
    (a) obtaining a dental x-ray image, wherein the dental x-ray image includes (i) at least a portion of the maxilla or mandible and (ii) an external standard for determining bone structure; and
    (b) analyzing the image obtained in step (a) to derive quantitative information on bone structure.

2. The method of claim 1, wherein the external standard comprises a calibration phantom that projects free of the mandible or maxilla.

3. The method of claim 2, wherein the calibration phantom comprises geometric patterns.

4. The method of claim 3, wherein the geometric patterns are plastic or metal.

5. The method of claim 4, wherein the geometric patterns are metal powder.

6. The method of claim 1, wherein step (b) comprises analyzing the image using one or more computer units.

7. The method of claim 6, wherein the analysis comprises identifying a region of anatomical interest in the image.

8. The method of claim 7, wherein the region of anatomical interest is in the mandible or the maxilla.

9. The method of claim 7, wherein the region of anatomical interest is a tooth.

10. The method of claim 1, wherein the method further comprises analyzing the image to obtain information on bone mineral density.

11. The method of claim 10, wherein the computer unit identifies structural or density information at a specified distance from the region of anatomical interest.

12. The method of claim 10, wherein the computer unit identifies areas in the image having selected structural or density characteristics.

13. The method of claim 12, wherein the selected density characteristic comprises the area of the image having the highest density.

14. The method of claim 12, wherein the selected density characteristic comprises the area of the image having the lowest density.

15. The method of claim 12, wherein the selected structural characteristic is selected from the group consisting of trabecular thickness; trabecular spacing; two-dimensional or three-dimensional spaces between trabecular; two-dimensional or three-dimensional architecture of the trabecular network.

16. The method of claim 1, wherein step (a) further comprises providing a hygienic cover adapted to receive the external standard.

17. The method of claim 16, wherein the hygienic cover is radiolucent.

18. The method of claim 16, wherein the hygienic cover is disposable.

19. The method of claim 16, wherein the hygienic cover is sterilizable.

20. The method of claim 16, wherein the external standard is integrated into the hygienic cover.

21. The method of claim 16, wherein the external standard is temporarily attached to the hygienic cover while obtaining the image.

22. The method of claim 16, wherein the hygienic cover further comprises a bolus in the path of the x-ray beam.

23. The method of claim 22, wherein the bolus is water-filled.

24. The method of claim 22, wherein the bolus is integrated into the hygienic cover.

25. The method of claim 22, wherein the bolus is temporarily attached to the hygienic cover.

26. The method of claim 6, wherein the computer unit includes one or more correction factors.

27. The method of claim 26, wherein the correction factors account for variation in soft-tissue thickness.

28. The method of claim 1, wherein obtaining the dental x-ray image further comprises compressing soft tissue in the image to a selected thickness.

29. The method of claim 1, wherein the x-ray image is an x-ray film.

30. The method of claim 16, wherein the hygienic cover is further adapted to receive x-ray film.

31. The method of claim 1, wherein the image is obtained digitally.

32. The method of claim 31, wherein the digital image is obtained using a selenium detector system or a silicon detector system.

33. An x-ray assembly for determining bone mineral density or bone structure comprising
    (a) a hygienic cover;
    (b) x-ray film and
    (d) a calibration phantom comprising at least one marker positioned in an area of known density or structure.

34. The assembly according to claim 33, wherein the hygienic cover is disposable.

35. The assembly according to claim 33, wherein the hygienic cover is sterilizable.

36. The assembly according to claim 33, wherein the calibration phantom is integrated into the hygienic cover.

37. The assembly of claim 33, wherein the assembly further comprises an x-ray film holder and the calibration phantom is temporarily attached to the x-ray film holder or to the hygienic cover.

38. The assembly of claim 33, wherein the calibration phantom comprises a plurality of geometric patterns that serve as a reference for bone structure characteristics.

39. The assembly of claim 38, wherein the bone structure characteristics are selected from the group consisting of trabecular thickness; trabecular spacing; two-dimensional or three-dimensional spaces between trabecular; two-dimensional and three-dimensional architecture of the trabecular network.

40. The assembly of claim 38, wherein the geometric patterns are made of metal, metal powder or plastic.

41. The assembly of claim 38, wherein the marker is a geometric pattern selected from the group consisting of circles, stars, squares, crescents, ovals, multiple-sided objects, irregularly shaped objects and combinations thereof.

42. The assembly of claim 33, wherein the film is integral to the hygienic cover.

43. The assembly of claim 33, wherein the calibration phantom is integral to the x-ray film.

44. The assembly of claim 43, wherein the calibration phantom is included between two of the physical layers of the x-ray film.

45. The assembly of claim 43, wherein the calibration phantom is included within one of the physical layers of the x-ray film.

46. The assembly of claim 33, wherein the hygienic cover further comprises a bolus.

47. The assembly of claim 46, wherein the bolus is integral to the hygienic cover.

48. The assembly of claim 46, wherein the bolus is temporarily attached to the hygienic cover.

49. The assembly of claim 33, wherein the calibration phantom is adapted to fit over one or more teeth.

50. The assembly of claim 49, wherein the calibration phantom is V-shaped or U-shaped.

51. A kit comprising a hygienic cover; a calibration phantom for bone structure or bone density comprising an integrated geometric pattern; an x-ray imaging assembly and computer programs, wherein said computer programs analyze and assess bone mineral density or bone structure.

52. A method of diagnosing a bone condition comprising analyzing a dental x-ray obtained by the method of claim 1.

53. The method of claim 52, wherein the condition is osteoporosis.

54. A method of treating a bone condition comprising diagnosing the condition according to the method of claim 43, and administering a suitable treatment.

55. The method of claim 54, wherein the condition is osteoporosis.

56. The method of claim 55, wherein the treatment comprises administering an anti-resorptive agent or an anabolic agent.

57. An x-ray assembly for determining bone mineral density or bone structure comprising
  (a) a hygienic cover,
  (b) x-ray film and
  (d) a calibration phantom for measuring bone mineral density or structure or combinations thereof.

58. The assembly according to claim 57, wherein the hygienic cover is disposable.

* * * * *

UNITED STATES PATENT AND TRADEMARK OFFICE
CERTIFICATE OF CORRECTION

PATENT NO. : 6,811,310 B2
DATED : November 2, 2004
INVENTOR(S) : Lang et al.

It is certified that error appears in the above-identified patent and that said Letters Patent is hereby corrected as shown below:

Column 21,
Line 43, please replace "cm" with -- *CM* --.
Line 62, please replace "e" with -- E --.
Line 66, please replace "e(i,j)" with -- E(i,j) --.

Column 23,
Line 44, please replace "roi" with -- ROI --.

Signed and Sealed this

Eighteenth Day of January, 2005

JON W. DUDAS
*Director of the United States Patent and Trademark Office*